(12) United States Patent
Yednock

(10) Patent No.: US 10,466,251 B2
(45) Date of Patent: Nov. 5, 2019

(54) METHODS OF TREATING INFLAMMATORY AND AUTOIMMUNE DISEASES WITH NATALIZUMAB

(75) Inventor: Theodore A. Yednock, Forest Knolls, CA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 13/425,058

(22) Filed: Mar. 20, 2012

(65) Prior Publication Data

US 2012/0177642 A1  Jul. 12, 2012

Related U.S. Application Data

(60) Provisional application No. 60/779,190, filed on Mar. 3, 2006.

(51) Int. Cl.
| | | |
|---|---|---|
| *A61K 39/395* | (2006.01) | |
| *C07K 16/28* | (2006.01) | |
| *G01N 33/68* | (2006.01) | |
| *A61K 39/00* | (2006.01) | |

(52) U.S. Cl.
CPC ... *G01N 33/6854* (2013.01); *A61K 39/39541* (2013.01); *C07K 16/2839* (2013.01); *C07K 16/2842* (2013.01); *A61K 2039/505* (2013.01); *A61K 2039/545* (2013.01); *Y02A 50/467* (2018.01)

(58) Field of Classification Search
None
See application file for complete search history.

(56) References Cited

U.S. PATENT DOCUMENTS

| | | |
|---|---|---|
| 5,840,299 A | 11/1998 | Bendig et al. |
| 6,033,665 A | 3/2000 | Yednock |
| 6,229,011 B1 | 5/2001 | Chen et al. |
| 6,238,859 B1 | 5/2001 | Luke et al. |
| 6,388,084 B1 | 5/2002 | Kaplan et al. |
| 6,551,593 B1 | 4/2003 | Ringler et al. |
| 6,602,503 B1 | 8/2003 | Lobb et al. |
| 6,605,602 B1 | 8/2003 | Vats |
| 7,008,949 B2 | 3/2006 | Konradi et al. |
| 7,026,328 B2 | 4/2006 | Konradi et al. |
| 7,026,501 B2 | 4/2006 | Kawaguchi et al. |
| 7,101,855 B2 | 9/2006 | Dressen et al. |
| 8,410,115 B2 | 4/2013 | Lieberburg |
| 9,493,567 B2 | 11/2016 | Lieberburg |
| 2002/0197233 A1 | 12/2002 | Relton et al. |
| 2003/0176498 A1 | 9/2003 | Kawaguchi et al. |
| 2004/0009169 A1 | 1/2004 | Taylor et al. |
| 2004/0138243 A1 | 7/2004 | Konradi et al. |
| 2004/0142954 A1 | 7/2004 | Konradi et al. |
| 2006/0009385 A1 | 1/2006 | Hoffman et al. |
| 2006/0013799 A1 | 1/2006 | Konradi et al. |
| 2007/0142416 A1 | 6/2007 | Semko et al. |
| 2007/0207141 A1* | 9/2007 | Lieberburg ........... 424/131.1 |
| 2007/0275481 A1* | 11/2007 | Vasilyeva et al. ........... 436/516 |
| 2008/0058357 A1 | 3/2008 | Smith et al. |
| 2009/0010926 A1* | 1/2009 | Panzara et al. ........... 424/133.1 |
| 2009/0169477 A1 | 7/2009 | Panzara et al. |
| 2009/0176256 A1* | 7/2009 | Subramanyam et al. ... 435/7.92 |
| 2009/0216107 A1 | 8/2009 | Rubin et al. |

FOREIGN PATENT DOCUMENTS

| | | |
|---|---|---|
| CA | 2236159 | 5/1997 |
| WO | WO 92/19774 A1 | 11/1992 |
| WO | WO 03/072040 A2 | 9/2003 |
| WO | WO 2006/107962 A2 | 10/2006 |
| WO | WO 2006/112951 A2 | 10/2006 |
| WO | WO 2007/041270 | 4/2007 |
| WO | WO 2007/100763 A2 | 9/2007 |
| WO | WO 2007/100770 A2 | 9/2007 |
| WO | WO 2007/101165 | 9/2007 |
| WO | WO 2007/103112 A2 | 9/2007 |

OTHER PUBLICATIONS

Abraham et al., "A Small-Molecule, Tight-binding Inhibitor of the Integrin α4β1 Blocks Antigen-induced Airway Responses and Inflammation in Experimental Asthma in Sheep," Am. J. Respir. Crit. Care Med., 162:603-611 (2000).

Agostini et al., "Genotype Profile of Human Polyomavirus JC Excreted in Urine of Immunocompetent Individuals," J. Clin. Microbiol. 34:159-164 (1996).

Albrecht et al., "Highly active antiretroviral therapy significantly improves the prognosis of patients with HIV-associated progressive multifocal leukoencephalopathy," AIDS, 12:1149-1154 (1998).

Baron et al., "Surface Expression of α4 Integrin by CD4 T Cells Is Required for Their Entry Into Brain Parenchyma," J. Exp. Med. 177:57-68 (1993).

Berger et al., "Predictive Factors for Prolonged Survival in Acquired Immunodeficiency Syndrome-Associated Progressive Multifocal Leukoencephalopathy," Ann. Neurol., 44:341-349 (1998).

Berger, Jr et al.: "Progressive multifocal leukoencephalopathy and natalizumab—Unforseen consequences"; New England Journal of Medicine 20050728; vol. 353, No. 4, Jul. 28, 2005, pp. 414-416.

Brennan, D.C., et al.; "Incidence of BK with tracrolimus versus cyclosporine and impact of preemptive immunosuppression reduction"; American Journal of Transplantation 200503 DK; vol. 5, No. 3, Mar. 2005, pp. 582-594.

(Continued)

Primary Examiner — Phillip Gambel
(74) Attorney, Agent, or Firm — David Goetz; Todd A. Lorenz

(57) ABSTRACT

Natalizumab is a safe and efficacious treatment for inflammatory and autoimmune diseases, such as multiple sclerosis, Crohn's Disease, and rheumatoid arthritis. Chain swapping between natalizumab and IgG4 molecules acts to reduce the level of bivalent natalizumab present following administration of natalizumab, and thus to lower the activity of natalizumab in the patient. Differences in IgG4 levels across patients or within a single patient across time may change the pharmacokinetic profile of natalizumab. Patients with lower levels of IgG4 may experience higher nadir levels of natalizumab during a dosing period. Monitoring IgG4 and/or bivalent natalizumab levels, and determining a dose or dosage period based on the monitoring may improve the safety and/or efficacy of natalizumab therapy.

18 Claims, No Drawings

(56) References Cited

OTHER PUBLICATIONS

Brooke et al., "Antibodies to CD44 and Integrin α4, but not L-selection, Prevent Central Nervous System Inflammation and Experimental Encephalomyelitis by Blocking Secondary Leukocyte Recruitment," Proc. Natl. Acad. Sci. 96:6896-6901 (1999).
Bruck et al., "Inflammatory Central Nervous System Demyelination: Correlation of Magnetic Resonance Imaging Findings with Lesion Pathology," Ann. Neurol., 42:783-793 (1997).
Clifford et al., "Haart Improves Prognosis in HIV-associated Progressive Multifocal Leokoencephalopathy," Neurology 52:623-625 (1999).
Collazos, "Opportunistic Infections of the CNS in Patients with AIDS," CNS Drugs 17:869-887 (2003).
Co-pending U.S. Appl. No. 11/711,874, filed Feb. 28, 2007.
Co-pending U.S. Appl. No. 11/713,000, filed Mar. 2, 2007.
Crowder et al., "Successful Outcome of Progressive Multifocal Leukoencephalopathy in a Renal Transplant Patient," American Journal of Transplantation, 5:1151-1158.
Demeter, "JC, BK, and Other Polyomaviruses; Progressive Multifocal Leukoencephalopathy," Mandell, Douglas and Bennett's Principles and Practice of Infectious Diseases, Mandell et al. Eds., 4th Ed., New York, NY: Churchill Livingstone; 1995:1400-1406.
Dörries et al., "Association of Human Polyomavirus JC with Peripheral Blood of Immunoimpaired and Healthy Individuals," Journal of NeuroVirology, 9(suppl. 1);81-87 (2003).
Dörries et al., "Infection of Human Polyomaviruses JC and BK in Peripheral Blood Leukocytes from Immunocompetent Individuals," Virology, 198:59-70 (1994).
Dubois et al., "Detection of JC Virus DNA in the Peripheral Blood Leukocytes of HIV-infected Patients," AIDS 10:353-358 (1996).
Dworkin, "A Review of Progressive Multifocal Leukoencephalopathy in Persons With and Without AIDS," Curr. Clin. Top. Infect. Dis. 22:181-195 (2002).
Engelhardt, et al. "Therapeutic targeting of α4-integrins in chronic inflammatory diseases: tipping the scales of risk towards benefit?" Eur. J. Immunol., 35:2268-2273 (2005).
Enns et al., Gastroenterology 126 (4, Suppl. 2): pA462 Apr. 2004.
Ernst et al., "Progressive Multifocal Leukoencephalopathy and Human Immunodeficiency Virus-associated White Matter Lesions in AIDS: Magnetization Transfer MR Imaging," Radiology 210:539-543 (1999).
Ferrante et al., "Detection of JC Virus DNA in Cerebrospinal Fluid from Multiple Sclerosis Patients," Multiple Sclerosis, 4:49-54 (1998).
Final Office Action dated Jul. 30, 2010, for U.S. Appl. No. 11/711,874.
Final Office Action dated Jul. 20, 2010 for U.S. Appl. No. 11/713,000.
Geschwind et al., "The Relative Contributions of HAART and Alpha-interferon for Therapy of Progressive Multifocal Leukoencephalopathy in AIDS," J. Neurovirol. 7:353-357 (2001).
Gibson et al., "Detection of JC Virus DNA in the Cerebrospinal Fluid of Patients With Progressive Multifocal Leukoencephalopathy," J. Med. Virol. 39:278-281 (1993).
Henson et al., "Amplification of JC Virus DNA from Brain and Cerebrospinal Fluid of Patients with Progressive Multifocal Leukoencephalopathy," Neurology 41:1967-1971 (1991).
Hijazi et al., "Pharmacokinetics, Safety, and Tolerability of R411, a Dual α4β1-α4β7 Integrin Antagonist After Oral Administration at Single and Multiple Once-Daily Ascending Doses in Healthy Volunteers," J. Clin. Pharmacol., 44:1368-1378 (2004).
Hochberg, "A Sharper Bonferroni Procedure for Multiple Tests of Significance," Biometrika 75:800-802 (1988).
Hoffmann et al., "Progressive Multifocal Leucoencephalopathy with Unusual Inflammatory Response During Antiretroviral Treatment," J. Neurol. Neurosurg. Psychiatry 74:1142-1144 (2003).
Hohlfeld et al., Seminars in Neurology 23:121-131, 2003.
Hurley et al., "Identification of HIV-Associated Progressive Multifocal Leukoencephalopathy: Magnetic Resonance Imaging and Spectroscopy," J. Neuropsychiatry Clin. Neurosci. 15:1-6 (2003).
IFNB Multiple Sclerosis Study Group, "Interferon Beta-1b is Effective in Relapsing-Remitting Multiple Sclerosis. I. Clinical Results of a Multicenter, Randomized, Double-blind, Placebo-controlled Trial,".
International Search Report for PCT/US06/06723 (I.e., WO 2006/112951 A2) dated Sep. 18, 2006.
International Search Report from PCT/US2007/004923, dated Sep. 22, 2008.
International Search Report from PCT/US2007/004943, dated Oct. 3, 2008.
International Search Report from PCT/US2007/05265, dated Oct. 2, 2007.
Isaac et al., "Multiple Sclerosis: A Serial Study Using MRI in Relapsing Patients," Neurology 38:1511-1515 (1988).
Jacobs et al., "Intramuscular Interferon Beta-1a for Disease Progression in Relapsing Multiple Sclerosis," Annals of Neurology, 39:285-294 (1996).
Johnson et al., "Copolymer 1 Reduces Relapse Rate and Improves Disability in Relapsimg-Remitting Multiple Sclerosis: Results of a Phase III Multicenter, Double-blind, Placebo-controlled Trial," Neurology 45:1268-1276 (1995).
Kappos et al., "Predictive Value of Gadolinium-enhanced Magentic Resonance Imaging for Relapse Rate and Changes in Disability or Impairment in Multiple Sclerosis: A Meta-analaysis," Lancet, 353:964-969 (1999).
Kent et al., "A Monoclonal Antibody to α4 Integrin Suppresses and Reverses Active Experimental Allergic Encephalomyelitis," J. Neuroimmunol. 58:1-10 (1995).
Khoury et al., "Longitudinal MRI in Multiple Sclerosis: Correlation Between Disability and Lesion Burden," Neurology 44:2120-2124 (1994).
Kieseier et al., Seminars in Neurology 23: 133-146, 2003.
Kitamura et al., "High Incidence of Urinary JC Virus Excretion in Nonimmunosuppressed Older Patients," J. Infect. Dis. 161:1128-1133 (1990).
Kleinschmidt-DeMasters et al., "Progressive Multifocal Leukoencephalopathy Complicationg Treatment with Natalizumab and Interferon Beta-1a for Multiple Sclerosis," N. Engl. J. Med. 353:369-374 (2005).
Knowles et al., "Prevalence of Long-Term BK and JC Excretion in HIV-Infected Adults and Lack of Correlation With Serological Markers," J. Med. Virol. 59:474-479 (1999).
Knowles et al., "The JC Virus Antibody Response in Serum and Cerebrospinal Fluid in Progressive Multifocal Leucoencephalophy," Clinical and Diagnostic Virology, 4:183-194 (1995).
Koralnik, "New Insights Into Progressive Multifocal Leukoencephalopathy," Current Opinion in Neurology, 17:365-370 (2004).
Kozovska et al., "Interferon Beta Induces T-helper 2 Immune Deviation in MS," Neurology 53:1692-1697 (1999).
Langer-Gould Annette, et al.: "Progressive multifocal leukoencephalopathy in a patient treated with natalizumab."; The New England Journal of Medicine; Jul. 28, 2005; vol. 353; No. 4; pp. 375-381.
Langer-Gould et al., "Progressive Multifocal ALeukoencephalopathy in a Patient Treated with Natalizumab," N. Eng. J. Med. 353:375-381 (2005).
Mamidi et al., "Central Nervous System Infections in Individuals with HIV-1 Infection," J. Neurovirol. 8:158-167 (2002).
McDonald et al., "Recommended Diagnostic Criteria for Multiple Sclerosis: Guidelines from the International Panel on the Diagnosis of Multiple Sclerosis," Ann. Neurol., 50:121-127 (2001).
McFarland et al., "The Role of MRI as a Surrogate Outcome Measure in Multiple Sclerosis," Multiple Sclerosis 8:40-51 (2002).
Miller et al., "A Controlled Trial of Natalizumab for Relapsing Multiple Sclerosis," N. Engl. J. Med. 348:15-23 (2003).
Molyneux et al., "Correlations between Monthly Enhanced MRI Lesion Rate and Changes in T2 Lesion Volume in Multiple Sclerosis," Ann. Neurol., 43:332-339 (1998).
Office Action dated Aug. 4, 2011, for U.S. Appl. No. 12/757,305.
Office Action dated Dec. 24, 2009, for U.S. Appl. No. 11/713,000.
Office Action dated Feb. 15, 2012, in copending U.S. Appl. No. 12/757,305.

(56) References Cited

OTHER PUBLICATIONS

Office Action dated Jul. 21, 2010, issued in co-pending U.S. Appl. No. 11/711,628.
Office Action dated Mar. 30, 2011 for U.S. Appl. No. 11/711,628.
Office Action dated Nov. 27, 2009, for U.S. Appl. No. 11/711,874.
Office Action dated Sep. 28, 2011 in copending U.S. Appl. No. 11/711,874.
Office Action dated Dec. 22, 2011, in U.S. Appl. No. 11/713,000.
Office Action dated Jul. 20, 2010, in U.S. Appl. No. 11/713,000.
Olsen et al., "White Matter Disease in AIDS: Findings at MR Imaging," Radiology 169:445-448 (1988).
Padgett et al., "Virologic and Serologic Studies of Progressive Multifocal Leukoencephalopathy," Prog. Clin. Biol. Res. 105:107-117 (1983).
Pestalozza et al. Multiple Sclerosis. 2005. vol. 11, pp. 390-394.
Polman et al., "A Randomized, Placebo-Controlled Trail of Natalizumab for Relapsing Multiple Sclerosis," N. Engl. J. Med., 354(9):899-910 (2006).
Post et al., "Progressive Multifocal Leukoencephalopathy in AIDS: Are There Any MR Findings Useful to Patient Management and Predictive of Patient Survival?," Am. J. Neuroradiol. 20:1896-1906 (1999).
PRISMS Study Group, "Randomised Double-blind Placebo-controlled Study of Interferon ß-1a in Relapsing/Remitting Multiple Sclerosis," Lancet 352:1498-1504 (1998).
Przepiorka et al., "Successful Treatment of Progressive Multifocal Leukoencephalopathy with Low-Dose Interleukin-2," Bone Marrow Transplant, 20:983-987 (1997).
Public Health Advisory—Suspended Marketing of Tysabri (Natalizumab), Feb. 28, 2005.
Redington et al., "Viral Infections of the Nervous System, 2002," Arch. Neurol: 59:712-718 (2002).
Rep et al., "Recombinant Interferon-β Blocks Proliferation but Enhances Interleukin-10 Secretion by Activated Human T-Cells," J. Neuroimmunol. 67:111-118 (1996).
Restriction Requirement dated Sep. 12, 2008 for U.S. Appl. No. 11/713,000.
Rudick et al., "Incidence and Significance of Neutralizing Antibodies to Interferon Beta-1a in Multiple Sclerosis," Neurology 50:1266-1272 (1998).
Rudick et al., "Natalizumab plus Interferon Beta-1a for Relapsing Multiple Sclerosis," N. Engl. J. Med., 354(9):911-923 (2006).
Salmaggi et al., "Reversal of CSF Positivity for JC Virus Genome by Cidofovir in a Patient with Systemic Lupus Erthematosus and Progressive Multifocal Leukoencephalopathy," Neurol. Sci. 22:17-20 (2001).
Schuurman et al., "Normal human immunoglobulin G4 is bispecific: it has two different antigen-combining sites," Immunology, 97:693-698 (1999).
Seth et al., "Advances in the Biology of JC Virus and Induction of Progressive Multifocal Leukoencephalopathy," J. Neurovirol. 9:236-246 (2003).
Shitrit et al.,"Progressive Multifocal Leukoencephalopathy in Transplant Recipients," Transpl. Int. 17:658-665 (2005).
Simon et al., "A Longitudinal Study of T1 Hypointense Lesions in Relapsing MS," Neurology 55:185-192 (2000).
Sundsfjord et al., "BK and JC Viruses in Human Immunodeficiency Virus Type 1-Infected Persons : Prevalence, Excretion, Viremia, and Viral Regulatory Regions," J. Infect. Dis. 169:485-490 (1994).
Tantisiriwat et al., "Progressive Multifocal Leukoencephalopathy in Patients with AIDS Receiving Highly Active Antiretroviral Therapy," Clin. Infect. Dis. 28:1152-1154 (1999).
Tenser, R.B. et al., "Natalizumab for Relapsing Multiple Sclerosis," New Engl. J. Med., 354(22): 2387-2389 (2006).
Thompson et al., " Major Differences in the Dynamics of Primary and Secondary Progressive Multiple Sclerosis," Ann. Neurol. 29:53-62 (1991).
Thompson et al., "Serial Gadolinium-Enhanced MRI in Relapsing/Remitting Multiple Sclerosis of Varying Disease Duration," Neurology 42:60-63 (1992).

Tornatore et al., "Detection of JC Virus DNA in Peripheral Lymphocytes from Patients with and without Progressive Multifocal Leukoencephalopathy," Ann. Neurol., 31:454-462 (1992).
Vago et al., "JCV-DNA and BKV-DNA in the CNS Tissue and CSF of AIDS Patients and Normal Subjects. Study of 41 Cases and Review of the Literature," J. Acquir. Imm. Defic. Syndr. Hum. Retrovirol. 12:139-146 (1996).
Van Assche et al. New England Journal of Medicine. Jul. 2005, vol. 353, No. 4, pp. 362-368.
Van Assche et al., "Physiological Basis for Novel Drug Therapies Used to Treat the Inflammatory Bowel Diseases: I. Immunology and therapeutic potential of antiadhesion molecule therapy in inflammatory bowel disease," Am. J. Physiol. Gastrointest. Liver Physiol., 288:G169-G174 (2005).
Van Assche et al., "Progressive Multifocal Leukoencephalophy after Natalizumab Therapy for Crohn's Disease," N. Eng. J. Med., 353:362-368 (2005).
Van Assche G et al.: "Progressive multifocal leukoencephalopathy after natalizumab therapy for Crohn's disease"; New England Journal of Medicine 20050728 US, vol. 353, No. 4, Jul. 28, 2005, pp. 362-368.
von Andrian et al., "α4 Integrins as Therapeutic Targets in Autoimmune Disease" N. Engl. J. Med., 348(1):68-72.
Weber et al., "Progressive Multifocal Leukoencephalopathy Disgnosed by Amplification of JC Virus-specific DNA from Cerebrospinal Fluid," AIDS 8:49-57 (1994).
Weber et al., "Specific Diagnosis of Progressive Multifocal Leukoencephalopathy by Polymerase Chain Reaction," J. Infect. Dis. 169:1138-1141 (1994).
Whitaker et al., "Outcomes Assessment in Multiple Sclerosis Clinical Trials: a Critical Analysis," Multiple Sclerosis, 1:37-47 (1995).
Willoughby et al., "Serial Magnetic Resonance Scanning in Multiple Sclerosis: A Second Prospective Study in Relapsing Patients," Ann. Neurol., 25:43-49 (1989).
Yednock et al., "Prevention of Experimental Autoimmune Encephalomyelitis by Antibodies Against α4β1 Integrin," Nature 356:63-66 (1992).
Yousry et al. "Evaluation of Patients Treated with Natalizumab for Progressive Multifocal Leukoencephalopathy," N. Engl. J. Med., 354:924-33 (2006).
Zang et al., "Regulation of Chemokine Receptor CCR5 and Production of RANTES and MIP-1α by Interferon-β," J. Neuroimmunol. 112:174-180 (2001).
Amendment and Response to OA, filed Mar. 31, 2016 in U.S. Appl. No. 12/757,305.
"BIOGEN IDEC and ELAN Announce Voluntary Suspension of TYSABRI®", Feb. 28, 2005 (Feb. 28, 2005), (//www.biogenidec.com/press_archive.aspx?ID=6015).
Bloomgren, G. et al. "Risk of Natalizumab-Associated Progressive Multifocal Leukoencephalopathy," N. Engl J Med., vol. 366, pp. 1870-1880 (2012).
Chaudhuri, A. "Lessons for clinical trials from natalizumab in multiple sclerosis," BMJ, vol. 332, pp. 416-419 (2006).
Engels et al., "Antibodies to JC and BK viruses among persons with non-Hodgkin lymphoma," Int. J. Cancer, vol. 117, pp. 1013-1019 (2005).
English Translation of excerpt from Japanese textbook entitled Immunology Illustrated, published on Feb. 10, 2000, 5th Edition, p. 102.
File History of U.S. Appl. No. 11/885,615, Amendment filed Nov. 22, 2010.
Food and Drug Administration Label for Tysabri®—Revised May 24, 2013.
Goelz et al., "Assay design and sample collection can affect anti-John Cunningham virus antibody detection," Ann. Neurol., vol. 69, No. 2 pp. 429-431 (2011).
Gorelik et al., "Anti-JC virus antibodies: implications for PML risk stratification," Am. Neurol. Assoc., vol. 68, pp. 295-303 (2010).
Knowles et al., "Comparison of cell culture-grown JC virus (primary human fetal glial cells and the JCI cell line) and recombinant JCV VP1 as antigen for the detection of anti-JCV antibody by haemagglutination inhibition," J. Virol. Methods, vol. 109, pp. 47-54 (2003).

(56) References Cited

OTHER PUBLICATIONS

Knowles et al., "Population-based study of antibody to the human polyomaviruses BKV and JCV and the Simian polyomavirus SV40," J. Med. Virol., vol. 71, pp. 115-123 (2003).
Knowles et al., "Prevalence of Long-Term BK and JC Excretion in HIV-Infected Adults and Lack of Correlation With Serological Markers," J. Med. Virol., vol. 59, pp. 474-479 (1999).
Ling et al., "The dynamics of herpesvirus and polyomavirus reactivation and shedding in healthy adults: a 14-month longitudinal study," J. Infect. Diseases, vol. 187, pp. 1571-1580 (2003).
Manji, H. and Miller, R.F., "Progressive multifocal leucoencephalopathy: progress in the AIDS era," J. of Neurosurgery & Psychiatry, vol. 69, pp. 569-571 (2000).
Raffel et al, "Assay Selction Affectws John Cunningham Virus Serostatus Classification in Multiple Sclerosis," Annals of Neurology vol. 72, No. 2, pp. 295-296 (2012).
Rollison et al., "Prediagnostic circulating antibodies to JC and BK human polyomaviruses and risk of non-Hodgkin lymphoma," Cancer Epidemiol. Biomarkers Prey., vol. 15, No. 3, pp. 543-550 (2006).
Sandborn et al., "Efficacy of Natalizumab in Maintaining Clinical Response and Remission in Crohn's Disease: Comparison of Sustained Response and Remission Rates Through 12 Months vs Point-In-Time Response and Remission Rates at Month 12," Gastroenterology, vol. 128, No. 4, Suppl. 2, p. A586 (2005).
Steinman, L. "Blocking adhesion molecules as therapy for multiple sclerosis: natalizumab," Nature Reviews/Drug Discovery 4:510-518 (2005).
Stolt et al., "Seroepidemiology of the human polyomaviruses," J. Gen. Virol., vol. 84, pp. 14991504 (2003).
Stone, John H., "IgG4-related disease: pathophysiologic insights drive emerging treatment approaches," Clin. Exp. Rheumatol. vol. (Suppl 98), pp. 1-3 (2016).
Weber et al., "Analysis of the Systemic and Intrathecal Humoral Immune Response in Progressive Multifocal Leukoencephalopathy," The Journal of Infectious Diseases, vol. 176, pp. 250-254 (1997).
Aalberse et al., "IgG4 breaking the rules", Immunology, vol. 105, No. 1, pp. 9-19 (2002).
Bitsch et al., "Acute axonal injury in multiple sclerosis Correlation with Demyelination and inflammation," Brain, vol. 123, pp. 1174-1183 (2000).
Bjartmar et al., "Axonal pathology in myelin disorders," J. Neurocytol., vol. 28, pp. 383-395 (1999).
Bjartmar, C. and Trapp, B.D., "Axonal and neuronal degeneration in multiple sclerosis: mechanisms and functional consequences,"Curr. Opin. Neurol., vol. 14, pp. 171-278 (2001).
Bomprezzi et al., "Extended interval dosing of natalizumab: a two-center, 7-year experience," Ther Adv Neurol Disord, vol. 7, No. 5, pp. 227-231 (2014).
Cannella, B. and Raine, D.S., "The Adhesion Molecule and Cytokine Profile of Multiple Sclerosis Lesions," Ann. Neurol., vol. 37, pp. 424-435 (1995).
Chabas et al., "The Influence of the Proinflammatry Cytokine, Osteopontin, on Augtoimmune Demyelinating Disease," Science, vol. 294, pp. 1731-1735 (2001).
Chang et al., "High incidence of JC viruria in JC-seropositive older individuals," J. Neurovirol., vol. 8, pp. 447-451 (2002).
Christensen et al., "a4 Integrin Directs Virus-Activated CD8+ T Cells to Sites of Infections," J. Immunol., vol. 154, pp. 5293-5301 (1995).
Dore-Duffy et al., "Expression of Endothelial Cell Activation Antigens in Microvessels from Pateints with Multiple Sclerosis," Frontiers in Cerebral Vascular Biology: Transport and Its Regulation, PLENUM, pp. 243-248 (1993).
Durez et al., Arthiritis Rheum., "Safety of Combination of Methotrexate (MTX) and Inflizimab (IFX) in a Large Legian Observational Patient Cohort with Refractory Rheumatoid Arthritis," vol. 46, No. 9S, p. 536 (2002).

Elices et al., "VCAM-1 on Activated Endothelium Interacts with the Leukocyte Integrin VLA-4 at a Site Distinct from the VLA-4/Fibronectin Binding Site," Cell, vol. 60, pp. 577-584 (1990).
Elphick et al., "The Human Polyomavirus, JCV, Uses Serotonin Receptors to Infect Cells," Science, vol. 306, pp. 1380-1383 (2004).
Ferguson et al., "Axonal damage in acute multiple sclerosis lesions," Brain, vol. 120, pp. 393-399 (1997).
Garrels et al., "Progressive Multifocal Leukoencephalopathy: Clinical and MR Response to Treatment," Am. J. Neuroradiol., vol. 17, pp. 597-600 (1996).
Hemler et al., "VLA Proteins in the Integrin Famiy: Structures, Functions, and Their Role on Leukocytesi" Annu. Rev. Immunol., vol. 8, pp. 365-400 (1990).
Holman et al., Progressive Muutifocal Leukoencephalopathy in the United States, 1979-1994: Increased Mortality Associates with HIV Infection, Neuroepidemiology, vol. 17, pp. 303-309 (1998).
IFNB MS Study Group, Neutralizing antidobies during treatment of multiple sclerosis with interferon beta-1b: Experience during the first three years, Neurology, vol. 47, pp. 889-894 (1996).
Inacio, P., URL: multiplesclerosisnewstoday.com/ 2018/02/05/actrims2018-ms-natalizumab-extended-interval-dosing-associatedreduction-progressive-multifocal- leukoencephalopathy-risk-touch-registry-data-suggest (2018).
Issekutz, Thomas B., "Lymphoctye homing to sites of inflammation," Curr. Opin. Immunol., vol. 4, pp. 287-293 (1992).
Kappos et al., "Neutralizing antidobies and efficacy of interferon β-1a," Neurology, vol. 65, pp. 40-47 (2005).
Kornek et al., "Multiple Sclerosis and Chronic Autoimmune Encephalomyelitis—A Comparative Quantitative Study of Aconal Injury in Active, Inactive, and Remyelinated Lesions," Amer. J. Pathalogy, vol. 157, No. 1, pp. 267-276 (2000).
Lobb, R.R. and Hemler, M.E., "The Pathophysiologic Role of α4 Integrins In Vivo," J. Clin. Invest., vol. 94, pp. 1731-1735 (1994).
Mire-Sluis et al., "Recommendations for the design and optimization of immunoassays used in the detection of host antibodies against biotechnology products," Journal of Immunological Methods, vol. 289, pp. 1-16 (2004).
Niino et al., "Natalizumab Effects on Immune Cell Responses in Multiple Sclerosis", Annals of Neurology, vol. 59, No. 5, pp. 748-754 (2006).
O'Neille, "Expression of vascular addressins and ICam-1 by endothelial cells in the spinal cord during chronic relapsing experimental allergic encephalomyelitis in the Biozzi AB/H mouse," Immunology, vol. 72, pp. 520-525 (1991).
Opposition to EP1991267 filed Sep. 20, 2018.
Oriordan et al., "The prognostic value of brain MRI in clinically isolated syndromes of the CNS," Brain, vol. 121, pp. 495-503 (1998).
Patton et al., "An acid dissociation bridging ELISA for detection of antibodies directed against therapeutic proteins in the presence of antigen", Journal of Immunological Methods, vol. 304, pp. 189-195 (2005).
Petterson et al., "VCAM-1-Positive Microglia Target Oligodendrocytes at the Border of Multiple Sclerosis Lesions," J. Neuropathy Exp. Neurol., vol. 61, No. 6, pp. 539-546 (2002).
Prisms Study Group, "PRIMSMS-4: Long-term efficacy of interferon-β-1α in relapsing MS," Neurology, vol. 56, pp. 1628-1636 (2001).
Raine et al., "Homing to Central Nervous System Vasculature by Antigen-Specific Lymphocytes—II. Lyphocyte/Endothelical Cell Adhesion during the Intitial Stages of Autoimmune Demyelination," Lab Invest. vol. 63, No. 4, pp. 476-489 (1990).
Rankin et al., "Progressive Multifocal Leukoencephalopathy in a Pateitn with Rheumatoid Arthritis and Polymyositis," J. Rheumatol, vol. 22, pp. 777-779 (1995).
Runmarker, B. and Andersen, O., "Prognostic factors in a multiple sclerosis incidence cohort with twenty-five years of follow-up," Brain, vol. 116, pp. 117-134 (1993).
Sailer et al., "Quantitative MRI in patients with clinically isolated syndromes suggestive of demyelination," Neurology, vol. 52, pp. 599-606 (1999).
Sponzilli et al., Progressive multifocal leukoencephalopath: A complication of immunosuppressive treatment, Neurology, vol. 25, pp. 664-668 (1975).

(56) References Cited

OTHER PUBLICATIONS

Springer, Timothy A., "Traffic Signals for Lymphocyte Recirculation and Leukocyte Emigration: The Multistep Paradigm," Cell, vol. 76, pp. 301-314 (1994).
Steffern et al., "Evidence for Involvement of ICAM-1 and VCAM-1 in Lymphocyte Interaction with Endothelium in Experimental Autoimmune Encephalomyelitis in the Central Nervous System in the SJL/J Mouse," Amer. J. Pathology, vol. 145, No. 1, pp. 189-201 (1994).
Trapp et al., "Axonal Transection in the Lesions of Myultiple Sclerosis," N.E. J. of Medicne, vol. 338, pp. 278-285 (1998).
Washington et al., "Expression of Immunologically Relevant Endothelial Cell Activation Antigens on Isolated Central Nervous System Microvessels from Patients with Multiple Sclerosis," Ann. Neurol., vol. 35, pp. 89-97 (1994).
Cohen et al., "A phase 2 study of Natalizumab in the subject with moderate to severe rheumatoid arthritis," ACR Annual Meeting; Nov. 10-15, 2006; Washington. Poster 497.

\* cited by examiner

METHODS OF TREATING INFLAMMATORY AND AUTOIMMUNE DISEASES WITH NATALIZUMAB

PRIORITY CLAIM

This application is a continuation application of U.S. patent application Ser. No. 11/713,000, filed Mar. 2, 2007, which claims priority to U.S. Provisional Patent Application No. 60/779,190, filed Mar. 3, 2006, the entire contents of which are hereby incorporated herein.

TECHNICAL FIELD

The invention relates to methods of treating inflammatory and autoimmune diseases with a recombinant antibody. These methods improve the safety of treatment by adjusting the dose based on IgG4 antibodies in the patient.

BACKGROUND ART

The migration of lymphocytes from the peripheral blood across the blood brain barrier has been reported to initiate the development of several central nervous system (CNS) inflammatory diseases. Lymphocyte entry into the CNS is mediated by cellular adhesion molecules (O'Neill et al., *Immunology* 72:520-525 (1991); Raine et al., *Lab. Invest.* 63:476-489 (1990); Yednock et al., *Nature* 356:63-66 (1992); Baron et al., *J. Exp. Med.* 177:57-68 (1993); Steffen et al., *Am. J. Path.* 145:189-201 (1994); Christensen et al., *J. Immunol.* 154:5293-5301 (1995)).

Cellular adhesion molecules present on the cell surface mediate the direct binding of one cell to another (Long et al., *Exp. Hematol.* 20:288-301 (1992)). The integrin and immunoglobulin supergene families of adhesion molecules regulate lymphocyte traffic into the CNS (Hemler et al., *Annu. Rev. Immunol.* 8:365-400 (1990); Springer et al., *Cell* 76:301-314 (1994); Issekutz et al., *Curr. Opin. Immunol.* 4:287-293 (1992)). Adhesion molecules have been widely reported to mediate inflammatory and autoimmune diseases, for example, asthma, Alzheimer's disease, atherosclerosis, AIDS dementia, diabetes, inflammatory bowel disease, multiple sclerosis, rheumatoid arthritis, tissue transplantation rejection, and tumor metastasis.

Integrins are heterodimers of non-covalently linked α and β chains (Hemler et al., *Annu. Rev. Immunol.* 8:365-400 (1990)). The α4β1 (also called very late activation antigen-4 VLA-4) and α4β7 integrins are present on the surface of most types of white blood cells, where they mediate white cell binding to endothelial cells by interacting with their cognate receptors, vascular cell adhesion molecule-1 (VCAM-1) and mucosal addressin cellular adhesion molecule-1 (MAdCAM-1), on the endothelial cell surface. Integrins are believed to play an important role in immune cell adhesion to the endothelial cell layer on blood vessels, facilitating their subsequent migration into inflamed tissues. Several studies implicate VLA-4 and, in particular the α4 integrin subunit, in CNS inflammation (Yednock et al., *Nature* 356:63-66 (1992); Baron et al., *J. Exp. Med.* 177: 57-68 (1993); Steffen et al., *Am. J. Path.* 145:189-201 (1994); Christensen et al., *J. Immunol.* 154:5293-5301 (1995). It has also been reported that VCAM-1 expression is elevated in inflamed brain tissue relative to normal brain tissue (Cannella and Raine, *Ann. Neurol.* 37:424-435 (1995); Washington et al., *Ann. Neurol.* 35:89-97 (1994); Dore-Duffy et al., *Frontiers in Cerebral Vascular Biology: Transport and Its Regulation,* 243-248 (Eds. Drewes & Betz, Plenum, N.Y. 1993)).

The interaction between α4β1 and its targets is a component of the inflammation that takes place in the CNS of patients with multiple sclerosis (MS). Under normal conditions, VCAM-1 is not expressed in the brain parenchyma. However, in the presence of pro-inflammatory cytokines, VCAM-1 is upregulated on endothelial cells and on microglial cells near the sites of inflammation (Elices et al., *Cell* 60:577-584 (1990); Lobb and Hemler, *J. Clin. Invest.* 94:1722-1728 (1994); Peterson et al., *J. Neuropathy Exp. Neurol.* 61:539-546 (2002)). Further, osteopontin, which exhibits many properties of a proinflammatory cytokine, is also upregulated in MS lesions (Chabas et al., *Science* 294:1731-1735 (2001)).

MS is a serious and disabling inflammatory and autoimmune disease of young adults, with a peak age of onset in the third decade of life. Most individuals present with the relapsing-remitting form of the disease and experience recurrent attacks, which, over time, result in accumulating permanent physical disability and cognitive decline. About 70% of these individuals will eventually enter a phase of progressive neurological decline (secondary progressive MS), with or without superimposed relapses. Current treatments are minimally effective for secondary progressive MS. The majority of patients suffer permanent neurological dysfunction and, on average, have a life expectancy of six to seven years after the onset of disease.

Currently, four therapies are approved in the United States for the treatment of relapsing forms of MS. The interferons, Betaseron® (interferon β-1b SC (subcutaneous)), AVONEX® (interferon β-1a IM (intramuscular)), and Rebif® (interferon β-1a SC), are cytokines with antiviral, antiproliferative, and immunomodulatory activities. Copaxone® (glatiramer acetate) is a mixture of synthetic polypeptides with a poorly understood mechanism of action. The β-interferonscan produce serious adverse events and some evidence suggests that copaxone is ineffective (Munari, et al., *The Cochrane Library,* Issue 1, Chichester, UK: John Wiley & Sons, Ltd. (2004)).

Serious adverse events of β-interferons include rare reports of hypersensitivity reactions, depression and suicide, decreased peripheral blood counts, hepatic injury, cardiomyopathy, and various autoimmune disorders (Betaseron Package Insert, 2003; Rebif Package Insert, 2004; AVONEX® Package Insert, 2005). The development of neutralizing antibodies to interferons is associated with a loss of efficacy. Antibodies that develop to a β-interferon cross-react with other interferons leading to loss of efficacy for the entire class in such patients (IFNB MS Study Group, *Neurology* 47:889-894 (1996); PRISMS Study Group, *Neurology* 56:1628-1636 (2001); Kappos et al., *Neurology* 65:40-47 (2005)). As a result, in the United States alone, over 50,000 patients who were previously treated no longer receive therapy. Thus, there is a large group of patients with active MS who are currently not receiving any approved therapy.

Among those patients who do receive treatment, a significant number continue to experience disease activity, as observed clinically and by magnetic resonance imaging (MRI). Although a variety of therapeutic strategies are currently used in clinical practice to manage breakthrough disease while on treatment (e.g., switching therapy, changing dose and frequency of interferon, combination therapy), the similar efficacy between available medications and lack of clinical data demonstrating the effectiveness of any of these strategies in breakthrough patients makes the decision of what to do for these patients largely empirical. Each of the partially effective approved medications leads to an approximately 30% reduction in relapse rate and limited impact on disability progression (IFNB MS Study Group, *Neurology* 43:655-661 (1993); Jacobs et al., *Ann. Neurol.* 39:285-289 (1996); PRISMS Study Group, *Lancet* 352:1498-1504 (1998)); Johnson et al., *Neurology* 45:1268-1276 (1995)). Data from the Phase 3 trials of β-interferon in MS show that 62% to 75% of subjects experienced at least one relapse during these 2-year trials despite interferon treatment (IFNB MS Study Group, *Neurology* 43:655-661 (1993); Jacobs et al., *Ann. Neurol.* 39:285-289 (1996); PRISMS Study Group, *Lancet* 352:1498-1504 (1998)). Similarly, 66% of subjects in the Phase 3 MS trial of glatiramer acetate experienced at least one relapse during the 2-year period, a proportion that was not significantly different from placebo (Johnson et al., *Neurology* 45:1268-1276 (1995)).

Progressive Multifocal Leukoencephalopathy (PML) is a severe, rapidly progressive disease that destroys the myelin coating which protects nerve cells. PML occurs almost exclusively in severely immunosuppressed patients and is frequently associated with lymphoproliferative and other chronic diseases, such as AIDS, Hodgkin's disease, chronic lymphocytic leukemia, sarcoidosis, tuberculosis, systemic lupus erythematosis, and organ transplantation. JC virus (JCV) is the etiological agent of PML and may result from a primary infection or follow reactivation of latent virus.

Natalizumab, an α4-integrin antagonist, has been used successfully to treat diseases with inflammatory and/or autoimmune components, for example, MS, Crohn's Disease, and rheumatoid arthritis. Natalizumab is a humanized $IgG_4\kappa$ monoclonal antibody directed against the α4-integrins α4β1 and α4β7. Chain swapping between natalizumab and other $IgG_4$ molecules may affect the pharmacokinetics of natalizumab. Differences in the concentration of $IgG_4$ between patients or within a patient over time may lead to differences in the concentration of bivalent natalizumab delivered over a dosing period. This may lead to variation in safety and/or efficacy between patients or within a patient over successive dosage periods.

Variation in $IgG_4$ levels may also lead to excessive natalizumab activity in certain patients. This may lead to an increased risk of infection in those patients. For example, there are three known cases of PML occurring during or after administration of natalizumab, two proved fatal and one patient recovered. All three cases occurred in patients on concomitant medications which may have contributed to immunosuppression.

Thus, there is a need in the art for determining the relationship between $IgG_4$ levels and natalizumab pharmacokinetics, and for adjusting natalizumab dose and dosage interval in certain patients in view of this information to improve the safety and/or efficacy of natalizumab treatment.

SUMMARY

The invention provides safer methods of using natalizumab to treat patients with inflammatory and autoimmune diseases.

In a first aspect, the invention provides a method of treating a patient with an inflammatory or autoimmune disease with natalizumab by administering a dose of natalizumab for a first dosage period; monitoring the amount of bivalent natalizumab in the patient's plasma or serum during the first dosage period; determining a second dose of natalizumab based on the level of bivalent natalizumab observed; and administering a second dose of natalizumab for a second dosage period; wherein the second dose improves the safety and/or efficacy of the treatment during the second dosage period. In an embodiment of the method the monitoring shows that the amount of bivalent natalizumab in the patient's plasma or serum remains above a predetermined level during the first dosage period, and the corrected dose of natalizumab administered over the second dosage period is designed to achieve a reduction of the natalizumab level during the second dosage period to below the predetermined level during at least a portion of the second dosage period. In an embodiment the second dose is lower than the first dose. In an embodiment the second dosage period is longer than the first dosage period. In an embodiment the corrected dose is lower than the first dose, and wherein the second dosage period is longer than the first dosage period. In an embodiment the first dose is 300 mg administered by IV infusion and the first dosage period is four weeks. In an embodiment the predetermined level is about 1 µg/ml, and wherein the second dose is less than 300 mg administered by IV infusion and the second dosage period is more than four weeks. In an embodiment the predetermined level is about 0.5 µg/ml, and wherein the second dose is less than 300 mg administered by IV infusion and the second dosage period is more than four weeks. In an embodiment the predetermined level is about 0.1 µg/ml, and wherein the second dose is less than 300 mg administered by IV infusion and the second dosage period is more than four weeks.

The invention also provides a method of treating a patient with an inflammatory or autoimmune disease with natalizumab, wherein the amount of bivalent natalizumab in the patient's plasma or serum falls below a predetermined level during the first dosage period within a predetermined time after administration of the first dose, and wherein the second dose of natalizumab administered over the second dosage period is designed to maintain the natalizumab level above the predetermined level.

In an embodiment of the method the disease is multiple sclerosis. In an embodiment the multiple sclerosis is selected from relapsing remitting, secondary progressive, primary progressive, and chronic progressive multiple sclerosis. In an embodiment of the method the disease is inflammatory bowel disease or rheumatoid arthritis. In an embodiment the inflammatory bowel disease is Crohn's Disease.

In an embodiment the method further includes monitoring the patient for indicators of serious infection and/or treating the patient with prophylaxis designed to reduce the risk of developing serious infection.

In an embodiment the method further includes monitoring the patient for indicators of progressive multifocal leukoencephalopathy. In an embodiment the monitoring detects JCV in the patient's urine, blood, and/or cerebrospinal fluid. In an embodiment the monitoring comprises serially removing samples of the patient's blood, measuring the amount of IgG antibodies to JCV in the samples, and comparing the amount of the antibodies in the samples. In an embodiment the monitoring further comprises measuring the amount of IgM antibodies to JCV in the samples, and comparing the amount of the IgM and IgG antibodies in the samples. In an embodiment the monitoring detects seroconversion and/or an increasing titer of JCV in the patient's urine and/or blood, and further includes removing a sample of the patient's cerebrospinal fluid when the comparison of the serial urine and/or blood samples detect seroconversion and/or an increasing titer of JCV; and testing the cerebrospinal fluid for the presence of JCV. In an embodiment the monitoring includes testing for clinical and/or radiologic symptoms of progressive multifocal leukoencephalopathy. In an embodiment the testing for clinical symptoms includes testing for new or worsening neurological symptoms. In an embodiment the neurological symptoms include one or more of central blindness, mental confusion, personality change, and dyskinesia. In an embodiment the testing for radiologic symptoms includes performing a Gd-enhanced magnetic resonance imaging scan. In an embodiment the method includes, in the presence of indicators of progressive multifocal leukoencephalopathy, providing at least one treatment selected from intravenous immunoglobulin therapy, plasmapheresis, and antiviral therapy. In an embodiment the antiviral therapy comprises the administration of at least one therapeutically effective dose of an antiviral agent selected from cytosine arabinoside (cytarabine), cidofovir, and a serotonin antagonist. In an embodiment the serotonin antagonist is a 5HT2a antagonist.

In an embodiment of the method the patient is not treated simultaneously with natalizumab and an immunosuppressive or antineoplastic agent. In an embodiment the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

In another aspect the invention provides a method of treating a patient with an inflammatory or autoimmune disease with natalizumab by determining the amount of IgG4 in the patient's plasma or serum; determining a dose and dosage period of natalizumab based on the amount of IgG4 in the patient's plasma or serum; and administering the dose of natalizumab to the patient over the dosage period; wherein the dose and dosage period improve the safety and/or efficacy of the treatment compared to the safety and/or efficacy provided by the standard dose and dosage period of natalizumab. In an embodiment of the method the standard dose is 300 mg by IV infusion and the standard dosage period is every four weeks. In an embodiment the amount of IgG4 in the patient's blood is below 200 μg/ml and the determined dose of natalizumab is below 300 mg by IV infusion. In an embodiment the amount of IgG4 in the patient's blood is below 200 ug/ml and the determined dosage period is longer than four weeks. In an embodiment the amount of IgG4 in the patient's blood is below 200 μg/ml, the determined dose of natalizumab is below 300 mg by IV infusion, and the determined dosage period is longer than four weeks. In an embodiment the amount of IgG4 in the patient's blood is below 100 μg/ml and the determined dose of natalizumab is below 300 mg by IV infusion. In an embodiment the amount of IgG4 in the patient's blood is below 100 ug/ml and the determined dosage period is longer than four weeks. In an embodiment the amount of IgG4 in the patient's blood is below 100 μg/ml, the determined dose of natalizumab is below 300 mg by IV infusion, and the determined dosage period is longer than four weeks. In an embodiment the amount of IgG4 in the patient's blood is below 15 μg/ml and the determined dose of natalizumab is below 300 mg by IV infusion. In an embodiment the amount of IgG4 in the patient's blood is below 15 ug/ml and the determined dosage period is longer than four weeks. In an embodiment the amount of IgG4 in the patient's blood is below 15 μg/ml, the determined dose of natalizumab is below 300 mg by IV infusion, and the determined dosage period is longer than four weeks. In an embodiment the amount of IgG4 in the patient's blood is below 200 μg/ml, the determined dose of natalizumab is below 300 mg by IV infusion, and the determined dosage period is shorter than four weeks. In an embodiment the amount of IgG4 in the patient's blood is below 100 μg/ml, the determined dose of natalizumab is below 300 mg by IV infusion, and the determined dosage period is shorter than four weeks. In an embodiment the amount of IgG4 in the patient's blood is below 15 μg/ml, the determined dose of natalizumab is below 300 mg by IV infusion, and the determined dosage period is shorter than four weeks.

In an embodiment of the method the disease is multiple sclerosis. In an embodiment the multiple sclerosis is selected from relapsing remitting, secondary progressive, primary progressive, and chronic progressive multiple sclerosis. In an embodiment of the method the disease is inflammatory bowel disease or rheumatoid arthritis. In an embodiment the inflammatory bowel disease is Crohn's Disease.

In an embodiment the method further includes monitoring the patient for indicators of serious infection and/or treating the patient with prophylaxis designed to reduce the risk of developing serious infection.

In an embodiment the method further includes monitoring the patient for indications of progressive multifocal leukoencephalopathy. In an embodiment the monitoring detects JCV in the patient's urine, blood, and/or cerebrospinal fluid. In an embodiment the monitoring comprises serially removing samples of the patient's blood, measuring the amount of IgG antibodies to JCV in the samples, and comparing the amount of the antibodies in the samples. In an embodiment the monitoring further comprises measuring the amount of IgM antibodies to JCV in the samples, and comparing the amount of the IgM and IgG antibodies in the samples. In an embodiment the monitoring detects seroconversion and/or an increasing titer of JCV in the patient's urine and/or blood, and further includes removing a sample of the patient's cerebrospinal fluid when the comparison of the serial urine and/or blood samples detect seroconversion and/or an increasing titer of JCV; and testing the cerebrospinal fluid for the presence of JCV. In an embodiment the monitoring includes testing for clinical and/or radiologic symptoms of progressive multifocal leukoencephalopathy. In an embodiment the testing for clinical symptoms comprises testing for new or worsening neurological symptoms. In an embodiment the neurological symptoms comprise one or more of central blindness, mental confusion, personality change, and dyskinesia. In an embodiment the testing for radiologic symptoms comprises performing a Gd-enhanced magnetic resonance imaging scan. In an embodiment the method further includes, in the presence of indicators of progressive multifocal leukoencephalopathy, providing at least one treatment selected from intravenous immunoglobulin therapy, plasmapheresis, and antiviral therapy. In an embodiment the antiviral therapy comprises the administration of at least one therapeutically effective dose of an antiviral agent selected from cytosine arabinoside (cytarabine), cidofovir, and a serotonin antagonist. In an embodiment the serotonin antagonist is a 5HT2a antagonist.

In an embodiment of the method the patient is not treated simultaneously with natalizumab and an immunosuppressive or antineoplastic agent. In an embodiment the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

In another aspect the invention provides a method of using natalizumab to treat a patient with an inflammatory or autoimmune disease by determining the amount of IgG4 in the patient's plasma or serum; administering a dose of natalizumab for a first dosage period; monitoring the level of bivalent natalizumab in the patient's plasma or serum during the first dosage period; determining a second dose and dosage period of natalizumab based on the amount of IgG4 in the patient's plasma or serum and on the level of bivalent natalizumab in the patient's plasma or serum; and administering the second dose of natalizumab for the second dosage period; wherein the second dose and dosage period improve the safety and/or efficacy of the treatment. In an embodiment of the method, the monitoring shows that the amount of bivalent natalizumab in the patient's plasma or serum remains above a predetermined level during the first dosage period, and the second dose of natalizumab administered over the second dosage period is designed to achieve a reduction of the natalizumab level during the second dosage period to below the predetermined level during at least a portion of the second dosage period. In an embodiment the first dose of natalizumab is 300 mg administered by IV infusion for a first dosage period of four weeks. In an embodiment the predetermined level is about 1 µg/ml. In an embodiment the predetermined level is about 0.5 µg/ml. In an embodiment the predetermined level is about 0.1 µg/ml. In an embodiment the amount of IgG4 in the patient's blood is below 200 µg/ml and the determined dose of natalizumab is below 300 mg by IV infusion. In an embodiment the patient's blood is below 200 ug/ml and the determined dosage period is longer than four weeks. In an embodiment the amount of IgG4 in the patient's blood is below 200 µg/ml, the determined dose of natalizumab is below 300 mg by IV infusion, and the determined dosage period is longer than four weeks. In an embodiment the amount of IgG4 in the patient's blood is below 100 µg/ml and the determined dose of natalizumab is below 300 mg by IV infusion. In an embodiment the amount of IgG4 in the patient's blood is below 100 ug/ml and the determined dosage period is longer than four weeks. In an embodiment the amount of IgG4 in the patient's blood is below 100 µg/ml, the determined dose of natalizumab is below 300 mg by IV infusion, and the determined dosage period is longer than four weeks. In an embodiment the amount of IgG4 in the patient's blood is below 15 µg/ml and the determined dose of natalizumab is below 300 mg by IV infusion. In an embodiment the amount of IgG4 in the patient's blood is below 15 ug/ml and the determined dosage period is longer than four weeks. In an embodiment the amount of IgG4 in the patient's blood is below 15 µg/ml, the determined dose of natalizumab is below 300 mg by IV infusion, and the determined dosage period is longer than four weeks. In an embodiment the standard dose of natalizumab is 300 mg IV infusion and the standard dosage period is four weeks.

In another embodiment of the method the corrected dose is lower than the first dose, or the second dosage period is longer than the first dosage period, or the corrected dose is lower than the first dose and the second dosage period is longer than the first dosage period. In an embodiment the amount of bivalent natalizumab in the patient's plasma or serum falls below a predetermined level during the first dosage period within a predetermined time after administration of the first dose, and wherein the second dose of natalizumab administered over the second dosage period is designed to maintain the natalizumab level above the predetermined level at least up to the predetermined time after administration of the second dose during the second dosage period.

In another embodiment the method further includes monitoring the patient for indicators of serious infection. In an embodiment the serious infection is progressive multifocal leukoencephalopathy. In an embodiment the method further includes treating the patient with prophylaxis designed to reduce the risk of developing serious infection. In an embodiment the serious infection is progressive multifocal leukoencephalopathy.

In another aspect the invention provides a method of using natalizumab to treat a patient with an inflammatory or autoimmune disease by determining the amount of IgG4 in the patient's plasma or serum prior to initiating treatment; initiating treatment of the patient with natalizumab in the event the amount of IgG4 in the patients plasma or serum is above a predefined threshold; and initiating treatment of the patient with natalizumab with increased monitoring for indicators of progressive multifocal leukoencephalopathy and/or opportunistic infections in the event the amount of IgG4 in the patients plasma or serum is at or below a predefined threshold; wherein determining of the amount of IgG4 in the patient's plasma or serum improves the safety and/or efficacy of the treatment. In an embodiment of the method the amount of IgG4 in the patients plasma or serum is at or below a second predefined threshold, treatment is not initiated. In an embodiment treatment is initiated if the amount of IgG4 in the patient's blood is about 200 µg/ml or higher. In an embodiment treatment is initiated if the amount of IgG4 in the patient's blood is about 100 µg/ml or higher. In an embodiment treatment is initiated if the amount of IgG4 in the patient's blood is about 15 µg/ml or higher.

In an embodiment the method further includes determining the amount of IgG4 in the patient's plasma or serum during treatment; and terminating treatment in the event the amount of IgG4 is the patients plasma or serum is below a predefined threshold. In an embodiment treatment is terminated if the amount of IgG4 in the patient's plasma or serum is about 200 µg/ml or lower. In an embodiment treatment is terminated if the amount of IgG4 in the patient's plasma or serum is about 100 µg/ml or lower. In an embodiment treatment is terminated if the amount of IgG4 in the patient's plasma or serum is about 15 µg/ml or lower.

In an embodiment the method further includes monitoring the amount of bivalent natalizumab in the patient's plasma or serum during treatment; and terminating treatment in the event the amount of bivalent natalizumab is above a predefined threshold. In an embodiment treatment is terminated if the amount of bivalent natalizumab in the patient's plasma or serum is about 1 µg/ml or higher. In an embodiment treatment is terminated if the amount of bivalent natalizumab in the patient's plasma or serum is about 0.5 µg/ml or higher. In an embodiment treatment is terminated if the amount of bivalent natalizumab in the patient's plasma or serum is about 0.1 µg/ml or higher.

In an embodiment the method further includes monitoring the amount of bivalent natalizumab in the patient's plasma or serum during treatment; and terminating treatment in the event the amount of bivalent natalizumab is above a predefined threshold. In an embodiment treatment is terminated if the amount of bivalent natalizumab in the patient's plasma or serum is about 1 µg/ml or higher. In an embodiment treatment is terminated if the amount of bivalent natalizumab in the patient's plasma or serum is about 0.5 µg/ml or higher. In an embodiment treatment is terminated if the amount of bivalent natalizumab in the patient's plasma or serum is about 0.1 µg/ml or higher. In an embodiment intravenous immunoglobulin is administered to the patient to reduce the level of bivalent natalizumab in the patient's plasma or serum. In an embodiment plasmapheresis therapy is administered to the patient to reduce the level of bivalent natalizumab in the patient's plasma or serum.

In another aspect the invention provides a method of treating a patient with an inflammatory or autoimmune disease with natalizumab by administering a dose of natalizumab for a first dosage period; monitoring the amount of bivalent natalizumab in the patient's plasma or serum during the first dosage period; determining a second dose of natalizumab based on the level of bivalent natalizumab observed; administering a second dose of natalizumab for a second dosage period; and administering the second dose of natalizumab for one or more subsequent second dosage periods; wherein the second dose improves the safety and/or efficacy of the treatment during the second dosage period.

In another aspect the invention provides a method of treating a patient with an inflammatory or autoimmune disease with natalizumab by determining the amount of IgG4 in the patient's plasma or serum; determining a dose and dosage period of natalizumab based on the amount of IgG4 in the patient's plasma or serum; administering the dose of natalizumab to the patient over the dosage period; and administering the dose of natalizumab to the patient over one or more subsequent dosage periods; wherein the dose and dosage period improve the safety and/or efficacy of the treatment compared to the safety and/or efficacy provided by the standard dose and dosage period of natalizumab.

In another aspect the invention provides a method of using natalizumab to treat a patient with an inflammatory or autoimmune disease by determining the amount of IgG4 in the patient's plasma or serum; administering a dose of natalizumab for a first dosage period; monitoring the level of bivalent natalizumab in the patient's plasma or serum during the first dosage period; determining a second dose and dosage period of natalizumab based on the amount of IgG4 in the patient's plasma or serum and on the level of bivalent natalizumab in the patient's plasma or serum; administering the second dose of natalizumab for the second dosage period; and administering the second dose of natalizumab for one or more subsequent second dosage periods; wherein the second dose and dosage period improve the safety and/or efficacy of the treatment.

DESCRIPTION OF THE INVENTION

Definitions

The terms used herein have their ordinary meanings, as set forth below, and can be further understood in the context of the specification.

A "patient" or "subject," used interchangeably herein, is a human unless otherwise indicated.

"Treatment" means any administration or application of remedies for disease and includes inhibiting the disease, arresting its development, and relieving the disease, for example, by causing regression, or restoring or repairing a lost, missing, or defective function or by stimulating an inefficient process.

"Terminating" means either a temporary or a permanent cessation.

"Dose" means the amount of natalizumab administered to a patient.

"Dosage period" means the time between the administration of a dose and the next successive administration of a dose. The dosage period may change with one or more further successive dose or doses, or may remain constant.

"Natalizumab" or "Natalizumab®" is a humanized antibody against VLA-4 as described in U.S. Pat. Nos. 5,840,299 and 6,033,665, which are herein incorporated by reference in their entireties. Also contemplated herein are other antibodies specific for VLA-4, including, but not limited to, immunoglobulins described in U.S. Pat. Nos. 6,602,503 and 6,551,593, and published U.S. Application No. 20020197233 by Relton et al. These antibody can be prepared by the methods disclosed in these documents, by mammalian cell expression systems, and by transgenic animal expression systems, for example, transgenic goats.

A "pharmaceutically effective amount" or "therapeutically effective amount," used interchangeably, is an amount sufficient to cure or at least partially arrest the symptoms of a disease and/or the complications of a disease.

A "serotonin antagonist" is any substance that decreases one or more effect of serotonin.

"Seroconversion" is the change of a serologic test from negative to positive, indicating the development of antibodies.

"Titer" is the concentration of an antibody in solution.

IgG4 Antibodies

Antibodies are proteins used by the immune system to identify and neutralize foreign objects like bacteria and viruses. Each antibody recognizes a specific antigen unique to its target. Immunoglobulins are glycoproteins in the immunoglobulin superfamily that function as antibodies. They are synthesized and secreted by plasma cells that are derived from the B cells of the immune system. B cells are activated upon binding to their specific antigen and differentiate into plasma cells. In some cases, the interaction of the B cell with a T helper cell is also necessary.

Immunoglobulins are heavy plasma proteins, often with added sugar chains on N-terminal (all antibodies) and occasionally O-terminal (IgA1 and IgD) amino acid residues. The basic unit of each antibody is a monomer. An antibody can be monomeric, dimeric, trimeric, tetrameric, pentameric, etc. The monomer is a "Y"-shape molecule that consists of two identical heavy chains and two identical light chains connected by disulfide bonds.

There are five types of heavy chain: γ, δ, α, μ and ε. They define classes of immunoglobulins. Heavy chains α and γ have approximately 450 amino acids, while μ and ε have approximately 550 amino acids. Each heavy chain has a constant region, which is the same by all immunoglobulins of the same class, and a variable region, which differs between immunoglobulins of different B cells, but is the same for all immunoglobulins produced by the same B cell. Heavy chains γ, α and δ have the constant region composed of three domains but have a hinge region; the constant region of heavy chains μ and ε is composed of four domains. The variable domain of any heavy chain is composed of one domain. These domains are about 110 amino acids long. There are also some amino acids between constant domains. There are only two types of light chain: λ, and κ. In humans, they are similar, but only one type is present in each antibody. Each light chain has two successive domains: one constant and one variable domain. The approximate length of a light chain is from 211 to 217 amino acids.

The monomer is composed of two heavy and two light chains. Together this gives six to eight constant domains and four variable domains. Enzymatic cleavage with papain creates two Fab (fragment antigen binding) fragments and an Fc (fragment crystallizable) fragment, whereas pepsin cleaves below hinge region, so a f(ab)2 fragment and a fc fragment is formed. Thus, each half of the forked end of the "Y"-shape monomer is called the Fab fragment. It is composed of one constant and one variable domain of each the heavy and the light chain, which together shape the antigen binding site at the amino terminal end of the monomer. The two variable domains bind the antigens they are specific for and that elicited their production.

The Fc fragment is composed of two heavy chains that each contribute two to three constant domains (depending on the class of the antibody). It binds to various cell receptors and complement proteins. In this way, it mediates different physiological effects of antibodies (opsonization, cell lysis, mast cell, basophil and eosinophil degranulation and other processes). The variable regions of the heavy and light chains can be fused together to form a single chain variable fragment (scFv), which retains the original specificity of the parent immunoglobulin.

Immunoglobulins are grouped into five classes, or isotypes, based on differences in heavy chain constant domains: IgG, IgA, IgM, IgD, and IgE. (The isotypes are also defined with light chains.) Other immune cells partner with antibodies to eliminate pathogens depending on which IgG, IgA, IgM, IgD, and IgE constant binding domain receptors it can express on its surface.

The antibodies that a single B lymphocyte produces can differ in their heavy chain and the B cell often expresses different classes of antibodies at the same time. However, they are identical in their specificity for antigen, conferred by their variable region. To achieve the large number of specificities the body needs to protect itself against many different foreign antigens, it must produce millions of B lymphocytes.

IgG is a monomeric immunoglobulin, built of two heavy chains γ and two light chains. Each molecule has two antigen binding sites. This is the most abundant immunoglobulin and is approximately equally distributed in blood and in tissue liquids. This is the only isotype that can pass through the placenta, thereby providing protection to the fetus in its first weeks of life before its own immune system has developed. It can bind to many kinds of pathogens, for example viruses, bacteria, and fungi, and protects the body against them by complement activation (classic pathway), opsonization for phagocytosis and neutralisation of their toxins. There are 4 subclasses: IgG1 (66%), IgG2 (23%), IgG3 (7%) and IgG4 (4%). IgG1, IgG3 and IgG4 cross the placenta easily. IgG3 is the most effective complement activator, followed by IgG1 and then IgG2. IgG4 does not activate complement. IgG1 and IgG3 bind with high affinity to Fc receptors on phagocytic cells. IgG4 has intermediate affinity and IgG2 affinity is extremely low.

Immunoglobulin G4 (IgG4) antibodies have been known for some time to be functionally monovalent. Recently, the structural basis for this monovalency has been elucidated: the in vivo exchange of IgG half-molecules (one H-plus one L-chain) among IgG4. This process results in bispecific antibodies that in most situations will behave as functionally monovalent antibodies. The structural basis for the abnormal behaviour of IgG4 seems to be largely the result of a single amino acid change relative to human IgG1: the change of a proline in core hinge of IgG1 to serine. This results in a marked shift in the equilibrium between interchain disulphide bridges and intrachain disulphide bridges, which for IgG4 results in 25-75% absence of a covalent interaction between the H-chains. Because of strong non-covalent interactions between the CH3 domains (and possibly also between the CH1 domain and the trans-CH2 domain) IgG4 is a stable four-chain molecule and does not easily exchange half-molecules under standard physiological conditions in vitro. The exchange may be catalysed in vivo by protein disulphide isomerase (PDI) and/or FcRn (the major histocompatibility complex (MHC)-related Fc receptor) during transit of IgG4 in the endosomal pathway in endothelial cells, or by an unknown mechanism. Because IgG4 is predominantly expressed under conditions of chronic antigen exposure, the biological relevance of this exchange of half-molecules is that it generates antibodies that are unable to form large immune complexes and therefore have a low potential for inducing immune inflammation. In contrast to monovalent immunoglobulin fragments, these scrambled immunoglobulins have a normal half-life. The significance of the ensuing bispecificity needs further evaluation, because this will be relevant only in situations where high IgG4 responses are found to two unrelated antigens that happen to be present in the body at the same time and place. In this context the significance of IgG4 autoreactivity might have to be re-evaluated. The main function of IgG4, however, is presumably to interfere with immune inflammation induced by complement-fixing antibodies, or, in the case of helminth infection or allergy, by IgE antibodies.

Most monoclonal antibodies consist of one type of L- and H-chain and have two identical antigen binding sites, which makes each monoclonal antibody molecule bivalent. In the case of IgG4, however, half-molecule exchange in vivo creates antibodies that are bispecifically monovalent. The experimental evidence supporting this view of IgG4 structure in vivo includes the observations that polyclonal IgG4 antibodies do not crosslink two antigens, i.e. are functionally monovalent; in contrast to polyclonal IgG4 antibody, monoclonal (chimeric) IgG4 antibody does crosslink two antigens; a substantial fraction of IgG4 (both monoclonal and polyclonal) lacks a covalent interaction between the heavy chains, but is maintained as a four-chain structure solely via non-covalent bonds; and bispecific antibodies can be found in plasma, which are mostly, if not exclusively, of the IgG4 type. Quantitatively, the level of bispecific reactivity can be predicted from the level of antigen-specific IgG4 antibodies.
Natalizumab Natalizumab is a recombinant humanized $IgG_4\kappa$ monoclonal antibody directed against the α4-integrins α4β1 and α4β7. Natalizumab contains human framework regions and the complementarity-determining regions of a murine antibody that binds to a4-integrin. The molecular weight of natalizumab is 149 kilodaltons.

Studies by Yednock and others have shown the clinical efficacy of α4-integrin blockade in experimental allergic encephalomyelitis (EAE), an animal model of MS (Yednock et al., *Nature* 1992; 356:63-66 (1992); Baron et al., *J. Exp. Med.* 177:57-68 (1993); Kent et al., *J. Neuroimmunol.* 58:1-10 (1995); Brocke et al., *Proc. Natl. Acad. Sci.* 96:6896-6901 (1999). These data demonstrated that α4-integrin blockade by a bound antibody can prevent leukocyte migration into the brain and thus support the hypothesis that α4-integrins are a target for MS therapeutics. In addition, these observations support the hypothesis that blockading leukocyte accumulation in the brain will prevent the local destruction of myelin, the insulating sheath covering nerve fibers, and neurons, which characterizes MS lesions. Natalizumab is the first antibody directed at this target and clinical data demonstrate the relevance of this treatment strategy.

Natalizumab is a member of an emerging class of agents known as the Selective Adhesion Molecule (SAM) Inhibitors. Natalizumab binding to α4β1 (also called VLA-4) and α4β7 integrins inhibits their molecular interactions with cognate integrin receptors on endothelial cells, VCAM-1 and MAdCAM-1, respectively. By inhibiting these molecular interactions, natalizumab prevents the recruitment and egress of leukocytes into sites of inflammation. A further mechanism of natalizumab action may be to suppress ongoing inflammatory reactions in diseased tissues by inhibiting the interaction of α4-expressing leukocytes with other ligands in the extracellular matrix (osteopontin and fibronectin) and on parenchymal cells, such as microglial cells (VCAM-1). As such, natalizumab may suppress ongoing inflammatory activity at the disease site and inhibit further recruitment of immune cells into inflamed tissues. Thus, treating MS patients with natalizumab may block entry of mononuclear leukocytes into the CNS and attenuate the inflammatory process that results in demyelination and axonal damage and ultimately provide clinical benefit by reducing the number of clinical relapses and the progression of disability, including motor, visual, and cognitive function.

Pharmacokinetics of Natalizumab

Following the repeat intravenous administration of a 300 mg dose of natalizumab to multiple sclerosis patients, the mean maximum observed serum concentration was 98±34 μg/mL. Mean average steady-state natalizumab concentrations over the dosing period were approximately 30 μg/mL. The mean half-life of 11±4 days was observed with a clearance of 16±5 mL/hour. The distribution volume of 5.7±1.9 L was consistent with plasma volume.

As measured in an in vitro receptor saturation assay, natalizumab, straight from the vial, saturates lymphocytes in whole blood at 0.3 to 1 ug/ml. This result is consistent with observations on cell adhesion, where stringent adhesion requires 1 ug/ml natalizumab. However, using the same assay to examine natalizumab in patient serum samples, receptor saturation appeared to require greater than 10 ug/ml. This effect may result from natalizumab swapping one of its IgG4 arms with other IgG4 antibodies in the serum in vivo, resulting in a loss of avidity and potency. Based on work with other single chain antibodies, this change could easily affect potency by 100-fold. Therefore, any meaningful natalizumab activity in the blood would most likely come from bivalent molecules remaining in the circulation after equilibrium was established with endogenous IgG4. Data indicates that this process appears to occur in a stoichiometric fashion over a relatively short period of time (hours to days). Thus, within hours or days the level of bivalent natalizumab present depends upon the starting level of endogenous IgG4.

A typical range for endogenous IgG4 is about 200 to 1000 ug/ml in humans. Based on calculations of the stoichiometry, when natalizumab is present at 10 ug/ml (the typical nadir blood level following a 300 mg dose administered IV over a four week dosage period), the level of bivalent natalizumab would range from 0.02 to 0.24 ug/ml at nadir levels (averaging 0.12 ug/ml). These values fit very well with the 75-85% receptor saturation levels observed with natalizumab in patient samples at nadir levels. Functional saturation with bivalent natalizumab occurs at 1 ug/ml. The level of bivalent natalizumab, however, increases significantly with lower levels of endogenous IgG4. For example, assuming a nadir level of natalizumab at 10 ug/ml, in a patient with 50 ug/ml of endogenous IgG4 the level of bivalent natalizumab would be ~1 ug/ml (or saturation). So patients with levels of endogenous IgG4 lower than about 50 ug/ml, for example, may have chronically saturating levels of natalizumab throughout the dosing period. At an IgG4 concentration of about 15 ug/ml the level of fully functional, bivalent natalizumab at nadir levels would be 2.5 ug/ml, well above receptor saturation. If an individual lacked IgG4 entirely, functional levels of natalizumab would be the same as the measured nadir levels, or about 10 ug/ml in a patient receiving a 300 mg dose by IV infusion over a four week dosing period.

As the exemplary calculations above make clear, a patient with a level of endogenous IgG4 equal to or below a certain level, such as about 200 ug/ml, about 100 ug/ml, about 50 ug/ml, about 15 ug/ml, or about zero would likely have a very different clinical profile with natalizumab than patients with normal levels of endogenous IgG4 (more that about 1 ug/ml functional antibody vs. 0.12 ug/ml).

These calculations also demonstrate that natalizumab exhibits strong efficacy even though concentrations drop below full occupancy levels for one or two weeks every month in typical patients, receiving a standard dose of 300 mg by IV infusion over a four week dosing period. This observation suggests that cell traffic into the CNS of typical patients is only partially inhibited during part of each dosing period. However, in a minority of patients, particularly those with low levels of endogenous IgG4, higher nadir levels of bivalent natalizumab may result in prolonged receptor saturation with natalizumab, resulting in complete inhibition of α4-integrins α4β1 and α4β7 for the dosing period and more profound inhibition cell trafficking. One consequence of this condition is that those patients are at a higher risk of serious infection while being treated with natalizumab.

Any factor that alters the nadir level of total natalizumab during a dosage interval will also affect the nadir level of bivalent, fully active natalizumab antibody. For example, in a patient with 100 ug/ml of endogenous IgG4, if nadir natalizumab levels are doubled, from 10 ug/ml to 20 ug/ml, then the level of bivalent antibody would triple, increasing from 0.5 ug/ml (below saturation) to 1.8 ug/ml (above saturation). Factors in addition to IgG4 levels that could affect the level of bivalent, fully active natalizumab antibody present during a dosing period include body weight, concomitant medication, and treatment duration. When using a fixed dose of natalizumab, differences in body weight can affect natalizumab levels by up to three-fold, e.g., 3 vs. 9 ug/ml or 6 vs. 16 ug/ml.

Although the effect of AVONEX® on pharmacokinetics is disputed, data derived from a small subset of patients indicate that nadir levels of natalizumab were 12 ug/ml with natalizumab alone (which is in line with all other studies) vs. 25 ug/ml when natalizumab is coadministered with AVONEX®. This is a difference that again, could triple the level of bivalent natalizumab molecules. Even if this effect isn't statistically significant for the population at large—if AVONEX® affects the upper limit of the range or nadir concentrations of natalizumab for even a small number of individuals, it could cause a significant change in the risk profile across the total population of patients.

Natalizumab may be administered repeatedly, such as at four week intervals. The number of prior doses of natalizumab may affect nadir levels experienced during each subsequent dosage interval. For example, concentration levels appear to increase with repeat dosing 5 ug/ml before dose number two vs. 12 ug/ml for dose number 15. Thus, Tysabri may accumulate with repeated dosing.

Methods of Treatment

Pharmaceutical compositions of natalizumab will be administered intravenously. The dose of natalizumab administered and the dosage period may be fixed across all or a class of patients or may be determined based on patient weight. For example, in an embodiment natalizumab is administered at a dose of from one to five mg per kg body weight by IV infusion. Alternatively, a fixed dose of natalizumab may be administered to all patients or to a class of patients independent of the body weight of the patients. For example, in an embodiment natalizumab is administered at a dose of 300 mg by IV infusion.

In an embodiment, the dose, either weight-based or fixed, is determined or adjusted based on the amount of bivalent natalizumab in the patient's plasma or serum and/or the amount of IgG4 in the patient's plasma or serum.

In an embodiment the amount of bivalent natalizumab in the patient's plasma or serum and/or the amount of IgG4 in the patient's plasma or serum are determined during a dosing period. The amount of bivalent natalizumab may be determined directly or may be determined or estimated indirectly, such as by measuring the amount of IgG4 and/or total natalizumab in the patient's plasma or serum and calculating or estimating the amount of bivalent natalizumab on the basis of those measurements.

In an embodiment the amount of IgG4 in the patient's plasma or serum may be used to determine a suitable dose and dosage period for administration of natalizumab, either prior to and/or after initiation of treatment. If the amount of IgG4 in the patient's blood is below 200 μg/ml, below 100 ug/ml, below 15 ug/ml, or lower, such as undetectable, the dose of natalizumab determined on the basis of the amount of IgG4 in the patient's plasma or serum may be lower than the standard dose or lower than the dose previously given to the patient. Also, the determines dosage period may be longer than the standard dosage period, or longer than one or more previously scheduled dosage periods. For example, the determined dose may be below 300 mg by IV infusion, the determined dosage period may be longer than four weeks, or the determined dose may be below 300 mg by IV infusion and the determined dosage period may be longer than four weeks.

In an embodiment the amount of bivalent natalizumab in a patient's plasma or serum during a first dosage period may be used to determine a second dose of natalizumab for administration for a second dosage period. For example, if the monitoring shows that the amount of bivalent natalizumab in the patient's plasma or serum remains above a predetermined level during the first dosage period, the corrected dose of natalizumab administered over the second dosage period can be designed to achieve a reduction of the natalizumab level during the second dosage period to below the predetermined level during at least a portion of the second dosage period. This can be achieved, for example, by determining a second dose lower than the first dose, a second dosage period longer than the first dosage period, or by determining a second dose lower than the first dose and a second dosage period longer than the first dosage period. For example, the predetermined level may be about 1 ug/ml, about 0.5 ug/ml, or about 0.1 ug/ml. The second dose of natalizumab may be below a standard dose and/or the determined dosage period may be longer than a standard dosage period. For example, the determined dose may be below 300 mg by IV infusion, the determined dosage period may be longer than four weeks, or the determined dose may be below 300 mg by IV infusion and the determined dosage period may be longer than four weeks.

ELISA Assays for Total and Bivalent Natalizumab

The amount of total natalizumab in a solution, for example a biological fluid such as plasma or serum, can be measured using an Enzyme-Linked Immunosorbant Assay (ELISA). The invention provides ELISA assays that measure both monovalent and bivalent natalizumab. Specifically, it provides solid-phase sandwich ELISAs for measuring the concentration of total natalizumab and the concentration of bivalent natalizumab. Generally, the ELISA assays described herein utilize antiidiotype antibodies specific for natalizumab and enzyme-linked antibodies to the Fc region of IgG4 antibodies.

In both the total natalizumab and bivalent natalizumab ELISAs, the antiidiotype antibody is bound to a solid surface. Any antiidiotype antibody specific for natalizumab is suitable for use in the ELISA. The antibody 12C4 is an example of an antiidiotype antibody specific for the natalizumab variable region and suitable for use in the assay. Suitable solid surfaces are well known in the art and include microtiter plates.

In the ELISA assay for total natalizumab, the antiidiotype antibody is bound to the surface at high density. In an embodiment, 12C4 is bound at a density of approximately 2 ug/ml. A fluid solution comprising an unknown quantity of natalizumab is added and allowed to interact with the antiidiotype antibody bound to the surface under conditions sufficient for natalizumab in the solution to bind to the antiidiotype antibody. The unbound portion of the solution is removed by washing the surface. The natalizumab which bound to the antiidiotype antibody is then detected using an antibody which is specific for the Fc region of IgG4 antibodies and is conjugated, directly or indirectly, to an enzyme. The surface is again washed to remove unbound enzyme-conjugated IgG4. A substrate for the enzyme is added and the reaction product is measured. The amount of reaction product correlates with the amount of natalizumab in solution. Suitable enzymes, substrates, and measuring devices are well-known in the art. In an embodiment, a commercially available antibody to IgG4 conjugated to alkaline phosphatase is used to detect bound natalizumab.

The amount of bivalent natalizumab can also be measured by solid phase sandwich ELISA using methods provided herein. An antiidiotype antibody is bound to a solid surface at low density. In an embodiment, 12C4 is bound to the surface at a density of approximately 0.3 ug/ml. A solution comprising an unknown quantity of natalizumab is allowed to interact as described above for the total natalizumab ELISA. The natalizumab is then detected with an antiidiotype antibody specific for bivalent natalizumab, which does not recognize either natalizumab monomers in solution or natalizumab monomers which has exchanged an IgG4 heavy chain with endogenous IgG4 and remain bound to the endogenous IgG4. The antiidiotype antibody used in the detection step is conjugated to a detectable enzyme. The antiidiotype antibody 12C4 is suitable for use in the bivalent natalizumab assay both as the solid phase bound antibody and/or as the detecting antibody. When used as the detecting antibody, 12C4 is conjugated to a detectable enzyme.

A wide variety of enzyme detection systems are known in the art. They include alkaline phosphatase conjugates, avidin and streptavidin conjugates, horseradish peroxidase conjugates, beta-galactosidase conjugates, and the like. A wide variety of substrates are also well known in the art and include 4-nitrophenylphosphate, 2-nitrophenyl-b-D-galactopyranoside, 2,2'-azino-di-[3-ethylbenzthiazoline sulfonate].

The concentration of both total and bivalent natalizumab in the serum of monkeys treated with natalizumab was determined using the ELISA assays of the invention. Natalizumab was measured 4, 24, and 72 hours after dosing with 3 mg/kg. The results of the 4 hr and 24 hr measurements are shown in Table 1. The acronym "blq" is used to denote that the result was below the limit of quantification. Serum spiked with 10 ug/ml natalizumab was used as a positive control.

TABLE 1

Total and Bivalent Serum Natalizumab Levels

| Animal | Experiment 1 4 hr | | Experiment 2 24 hr | | Experiment 3 |
|---|---|---|---|---|---|
| | Total Nat. | Bivalent Nat. | Total Nat. | Bivalent Nat. | Bivalent Nat. |
| 1 | 56.1 | 37.3 | 17.4 | 48.3 | 16.7 |
| 2 | 53.0 | 32.6 | 14.1 | 1.0 | 0.5 |
| 3 | | | 21.1 | 47.0 | 16.9 |
| 4 | 66.8 | 31.0 | 10.8 | 0.3 | 1.8 |
| 5 | 65.4 | 38.0 | 19.8 | 41.7 | 15.2 |
| 6 | | | 8.9 | 0.5 | 0.3 |
| 7 | 54.6 | 30.0 | 7.3 | blq | 0.2 |
| 8 | 53.0 | 27.8 | 9.6 | blq | 0.2 |
| 9 | | | 17.3 | 14.2 | 5.4 |
| 10 | 54.1 | 37.4 | 12.9 | 29.0 | 6.1 |
| 11 | 57.4 | 28.5 | 10.1 | 0.4-3 | 0.2 |
| 12 | | | 18.7 | 35.2 | 18.7 |

Safety of Natalizumab

The safety of natalizumab is demonstrated herein, based on results of treating 3,919 subjects with natalizumab in clinical trials for MS, Crohn's Disease, and rheumatoid arthritis, resulting in 5,505 patient-years of natalizumab exposure. Treatment with natalizumab was generally well tolerated. Eighteen treatment-emergent deaths occurred in the entire natalizumab program. The adverse events encountered in the trials, both common and serious, were similar in natalizumab-treated patients and controls. Adverse events that led to discontinuation of natalizumab occurred in 5.8% of natalizumab-treated MS patients and in 4.8% of placebo-treated MS patients, with urticaria being the most common cause of discontinuation in the natalizumab-treated patients (1.2%).

Like other highly active drugs used to treat autoimmune diseases, natalizumab is not without risk. Unfortunately, with the clinical efficacy of immunomodulatory agents such as natalizumab comes the risk of significant mechanism-based side effects. The risks of medications that modulate immune function in order to treat serious chronic diseases have been well recognized over the past several years. Medicines such as the TNFα antagonists (e.g., infliximab, adalimumab, and etanercept) are potent modulators of immune function and are approved for numerous serious autoimmune diseases such as rheumatoid arthritis, Crohn's Disease, psoriasis, psoriatic arthritis, and ankylosing spondylitis. Although very effective, these agents are associated with serious adverse events, particularly infections that have been associated with significant morbidity and mortality.

The invention provides the identification, through detailed safety analyses, of PML as a rare, but significant, risk of natalizumab treatment. In addition, serious non-PML opportunistic infections have been observed in natalizumab-treated patients, mostly in Crohn's Disease patients in association with concurrent immunosuppressant use or other significant co-morbidities. In addition, we have identified patient populations in whom the benefit-risk profile is less well defined. The occurrence of these infections highlights the need for a comprehensive risk management program in the post-marketing setting focused on appropriate use conditions and assessment and minimization of the risk of PML and other serious opportunistic infections.

Deaths

Of the eighteen deaths that occurred during the clinical trials, five occurred in the placebo-controlled MS trials, including two in patients who had received natalizumab and three who had received placebo). The patients who received natalizumab died of alcohol intoxication and metastatic malignant melanoma. The patients who received placebo died of cardiac arrest, respiratory arrest, and pleural carcinomatosis with seizures. Four deaths occurred in the open-label MS trials, due to respiratory distress, PML, suicide, and seizure due to MS.

Six deaths of natalizumab-treated Crohn's Disease patients were observed in the trials. The exposure to natalizumab was approximately three-fold greater in these trials than exposure to placebo. The causes of death were acute myocardial infarction, acute renal failure, carbon dioxide asphyxiation, PML, *Pneumocystis carinii* pneumonia, and bronchopulmonary aspergillosis.

Three deaths occurred in the rheumatoid arthritis trials, two in natalizumab-treated patients and one in a patient treated with a placebo. The natalizumab-treated patients died of hemoptysis with respiratory failure and end-stage rheumatoid pulmonary disease. The placebo-treated patient died of circulatory and respiratory insufficiency.

In the MS studies, apart from PML, no other safety signal was apparent from the study deaths. In the Crohn's Disease studies, one patient died from PML. Two additional deaths in Crohn's Disease were associated with opportunistic infections, namely, bronchopulmonary aspergillosis and *Pneumocystis carinii* pneumonia. These patients had significant co-morbidities, which may have contributed to the development of these infections.

Adverse Events

At least one serious adverse event was encountered by 251 of the 1,617 natalizumab-treated MS patients (15.5%) and by 214 of the 1,135 placebo-treated MS patients (18.9%) in the placebo-controlled trial. The most common serious adverse events, classified by organ systems, were nervous system disorders (5.9% natalizumab, 10.2% placebo). MS relapse contributed significantly to this incidence (4.7% natalizumab, 9.0% placebo). The second most common serious adverse events were infections and infestations (2.4% natalizumab, 2.2% placebo), with appendicitis and urinary tract infection (<1% in both groups) as the most common.

The incidence of hypersensitivity reactions, an event expected to result from treatment with therapeutic proteins, was approximately 4% with serious systemic reactions occurring at an incidence of less than 1%. The reactions tended to occur early in the treatment course, but were observed throughout the course of infusion. Although the specific mechanisms of the reactions have not been determined, clinically, the reactions appeared to be typical IgE- or IgG-mediated immediate-type hypersensitivity reactions. All patients recovered without sequelae.

The occurrence of malignancy during natalizumab treatment was uncommon. The incidence of malignancy was balanced between the natalizumab and control groups. The rates of malignancies observed during natalizumab treatment were within the expected rates per comparison with the existing cancer registries, such as the National Cancer Institute's Surveillance Epidemiology and End Results.

Evaluation of PML Cases

Three confirmed cases of PML have been identified, two of which were fatal. Two cases occurred in MS patients and one in a patient with Crohn's Disease. Both MS patients received natalizumab for over two years in addition to AVONEX®. The Crohn's Disease patient received eight doses of natalizumab over an 18-month period and was immunocompromised due to chronic azathioprine use as manifested by persistent lymphopenia. All three PML patients presented with subtle clinical changes early in their disease course that were noted by the patients or their families.

The first patient to contract a fatal case of PML was a 46-year-old female with MS who presented to her neurologist with right-sided paresthesia and dysesthesia, and right upper extremity clumsiness. MRI brain scanning demonstrated four non-enhancing T2-hyperintense lesions bilaterally in the corona radiata. Six weeks later, she presented with new blurring of the vision in her right eye. Visual acuity was 20/15 in the left eye and 20/100 in the right. Spinal fluid analysis yielded one white blood cell, normal protein and glucose, and no oligoclonal bands. A follow-up MRI brain scan revealed two new subcortical lesions in the right parietal region that were hyperintense on FLAIR imaging and hypointense on T1.

AVONEX® treatment was initiated, but she subsequently suffered three relapses, the most recent of which involved band-like pain around the abdomen, lower extremity weakness, and spasticity requiring treatment with methylprednisolone. Her Expanded Disability Status Scale (EDSS) score in prior to entry into the placebo-controlled MS study, as described in more detail below, was 2.5. She received 30 infusions of natalizumab before entering the open-label extension study and receiving an additional seven infusions. She had no exacerbations or suspected relapses during her time in the placebo-controlled study. She developed five new or enlarging T2-hyperintense lesions during the first year of the placebo-controlled study and one during the second year. She was negative for anti-natalizumab antibodies and her serum concentration of natalizumab was similar to the mean of the study populations throughout her participation.

In November 2004, she began to experience motor dysfunction, and cognitive and language difficulties, which progressed to right hemiparesis by the following month. An MRI brain scan performed in December 2004 revealed left frontal T2-hyperintensity and T1-hypointensity with extension into the centrum semiovale and corona radiata without Gd-enhancement. She received two courses of high dose steroids over the next few months, but continued to decline. She received her last dose of natalizumab on Jan. 18, 2005. She was readmitted to the hospital on Feb. 12, 2005 with worsening clinical status. A repeat MRI brain scan in February 2005 showed extension of the lesion seen previously. An extensive work-up over the next week revealed JC viral DNA in the CSF, resulting in the diagnosis of PML. She died on Feb. 24, 2005. Post-mortem examination revealed normal organs without evidence of opportunistic infection. The brain examination revealed extensive, severe cavitation mainly in the left hemisphere as well as multiple non-cavitated, ovoid areas throughout the white matter of both hemispheres typical of PML, having reactive astrocytes with enlarged, hyperchromatic nuclei (Kleinschmidt-DeMasters and Tyler, N. Engl. J. Med. 353:369-374 (2005)).

The second patient is a 46-year-old male who experienced his first symptoms of relapsing/remitting MS in 1983. His past medical history is significant for auricular zoster, Ramsay-Hunt syndrome, and melanoma. His family history is notable for a sister with MS. He had been treated with AVONEX® since 1998, and experienced three relapses the year before enrolling in the placebo-controlled MS study, during which he experienced no relapses or evidence of progression. He was negative for anti-natalizumab antibodies and his serum concentration of natalizumab was similar to the mean of the study populations throughout his participation.

In October 2004, his MRI scan showed a small periventricular Gd-enhancing lesion on the right and a small right frontal, subcortical, non-enhancing, T2-hyperintense lesion. In November 2004, he exhibited behavioral changes followed by hemiparesis and cognitive impairment. His last dose of natalizumab was in December 2004. In February 2005, despite treatment with high dose intravenous methylprednisolone, he continued to deteriorate. A brain MRI scan in February 2005 demonstrated extension of the previously identified lesion. He underwent an extensive work-up, including CSF analysis and brain biopsy, which resulted in the diagnosis of PML. Cidofovir treatment was initiated without clinical effect. The JC viral load decreased in his plasma and CSF over the next few months. This corresponded to further deterioration in his clinical course and development of Gd-enhancing lesions on MRI, consistent with Immune Reconstitution Inflammatory Syndrome. He continued to receive treatment with cidofovir, and cytarabine was added. Approximately 3 months following discontinuation of natalizumab, he began to improve. He is able to converse and can hold high-level conversations about his medical course and treatment, but has significant residual cognitive impairment with left hemiparesis and ataxia (Langer-Gould et al., N. Eng. J. Med. 353:375-381 (2005)).

The final patient was a 60-year-old male with a 28-year history of Crohn's Disease. Over the course of his illness, he had been treated with azathioprine, oral budesonide, corticosteroids, and four doses of infliximab. He displayed pre-existing signs of impaired hematopoiesis, predominantly lymphopenia and anemia, since 1996 and received azathioprine beginning in 1999. He was enrolled in a Phase 3 study of natalizumab in patients with active Crohn's Disease in March 2002 and received three doses concomitantly with azathioprine prior to being randomized to placebo in a Phase 3 maintenance study. He remained on azathioprine and placebo until November 2002 when azathioprine was discontinued due to refractory pancytopenia. In February 2003, he began open-label treatment with natalizumab. He was negative for anti-natalizumab antibodies and his serum concentration of natalizumab was similar to the mean of the study populations throughout his participation.

In July 2003, one month after his fifth dose of natalizumab, he presented with a one-week history of cognitive decline. A brain MRI scan demonstrated a large T2-hyperintense lesion in the right frontal lobe, and additional hyperintense lesions in the left frontal and temporal lobes that did not enhance with gadolinium. He underwent a partial resection of the lesion, the pathology of which was read at the time as an anaplastic astrocytoma, WHO Grade III. He was treated with corticosteroids and anticonvulsants, but was too ill for radiation therapy. Follow-up MRI six weeks after surgery showed tumor extension. He deteriorated clinically and died in December 2003. The case was reported by the treating physician as a malignant astrocytoma, based upon the final pathology report. In February, as a result of the one confirmed and one suspected case of PML described above, his case was reassessed and determined to be PML following consultation with two independent neuropathologists with expertise in PML (Van Assche et al., *N. Engl. J. Med.* 353:362-368 (2005)).

Clinical trial patients exposed to natalizumab were systematically assessed for evidence of incipient PML or any other opportunistic infection. Patients were evaluated if they had any active neurological deterioration for which PML could not be excluded as a diagnosis, showed MRI abnormalities for which PML could not be ruled out, or their CSF had detectable JCV DNA titers.

Criteria were established prospectively for the neuroradiologic evidence and laboratory assays for the diagnosis of PML. A diagnosis of "confirmed PML" was defined by presence of progressive clinical disease, MRI signs typical of PML, detection of JCV DNA in CSF, or pathologic confirmation. Sufficient evidence to exclude PML was defined as lack of progressive neurological disease, MRI lesions not typical of PML or stable over time, or no detectable JCV DNA in the CSF if the MRI was suspicious. A case was deemed "indeterminate" if there was clinical or MRI suspicion of PML and follow-up clinical, MRI, or CSF data could not be obtained.

A total of 3,826 eligible study participants (2,248 MS patients, and 1,578 Crohn's Disease/rheumatoid arthritis patients) were notified to report to their treating physician/investigators for an assessment. Investigators were requested to perform the assessment procedure, including medical history, neurological examination, brain MRI, and CSF collection. Blood samples were also collected for PCR analysis of JCV DNA as an exploratory adjunct. MRI scans were assessed by Central Reader Centers with expertise in neurological disorders, including the two Central Reader Centers for the original Phase 3 MS studies. A consensus guideline was developed prospectively to standardize criteria to help distinguish MS white matter abnormalities from those of PML.

In all, 3,389 (89%) study patients with MS, Crohn's Disease, or rheumatoid arthritis were assessed by their treating physician, 3,116 of whom had received natalizumab. The remaining 273 patients had received placebo as part of a clinical trial and were included as a control group. Of the 437 that were not assessed, 60 (22 MS patients, 38 Crohn's Disease/rheumatoid arthritis patients) were lost to follow-up. Amongst the 3,389 patients who participated, 2,046 were MS study patients, over 97% of whom were seen within three months of their last natalizumab dose. Six MS patients were referred for further evaluation. Of these clinical trial patients, five were referred due to neurological worsening and one due to possible PML based on MRI findings. MRI scan review effectively ruled out the diagnosis of PML in the five patients referred based on clinical concern. Repeat MRI and CSF analysis excluded PML in the case referred based on MRI findings.

Of the 1,349 Crohn's Disease/rheumatoid arthritis patients who participated in the safety evaluation, 21% were seen within three months of their last dose, 91% within six months. Thirty-five patients were evaluated, including one due to clinical or neurological symptoms, 32 based on suspicious changes on MRI, one due to high plasma JCV copy number, and one due to an inability to perform MRI in a patient with a normal neurological examination. The higher rate of examination of Crohn's Disease compared to MS was predominantly driven by the lack of baseline MRI scans for comparison in the Crohn's Disease population. Most cases were deemed not to be PML based on review of neurological examination, MRI and, if available, CSF testing. For the ten cases in which concern still remained, repeat MRI assessments were performed and all were diagnosed as "not PML" based on lack of clinical progression, lack of MRI progression over two months following the initial MRI leading to referral for evaluation, and in some cases, results of CSF testing.

MRI scans of the brain with and without Gd-enhancement and a FLAIR sequence were sometimes a useful tool for excluding a diagnosis of PML in the MS cases. The existence of pre-treatment and on-treatment MRI scans increased specificity and assisted in interpretation of the follow-up MRI scans obtained at varying time points, especially in the setting when the patient's neurological condition was worsening. During the safety evaluation process, comparison to previous scan was required in approximately 35% percent of MS cases because of the presence of lesions for which PML could not be definitely excluded. After comparison to a prior scan, the neuroradiologist was able to exclude PML in greater than 99% of MS cases.

CSF was available for testing in 396 patients who had been treated for MS or Crohn's Disease with natalizumab. JCV was not detected in any of these cases, including 19 patients evaluated based on clinical or MRI criteria. Samples from 411 patients with MS and other neurological disorders served as CSF and plasma controls and were evaluated in collaboration with the Karolinska Institute and the National Institutes of Health (Yousry et al., *N. Engl. J. Med.* scheduled for publication Mar. 2, 2006). No detectable JCV was found in these CSF samples, confirming the specificity of the CSF assay for only active cases of PML. Each of the three patients with confirmed PML had detectable JCV DNA. A previous study had indicated that JCV was found in 11% of the biological specimens of the 121 MS patients tested (Ferrante et al., *Multiple Sclerosis* 4:49-54 (1998)).

Plasma was tested for the presence of JCV DNA as an exploratory measure. The entire consenting study population (2,370 patients) was evaluated using a high-throughput automated system of DNA extraction and PCR analysis. In addition, a random subset of samples was assessed using a manual low-throughput method. Although the manual method was demonstrated to be an order of magnitude more sensitive than the high-throughput system, given the techniques involved, testing using this method was only possible in approximately 10% of the overall population (209 patients). Of the 2,370 patients from the safety evaluation who were tested for JC viremia, only five patients (0.2%) had detectable JCV DNA, three of whom had never received natalizumab. In addition, JCV DNA was not detected in any of the 411 samples from MS patients naïve to treatment and patients with other neurological diseases. These results were confirmed using the manual extraction method. In addition, of the random subset of 209 patients tested by the manual method, an additional five (2.4%) samples had detectable JCV DNA. None of the patients with detectable JCV DNA in their plasma by either method had clinical features or MRI findings suggestive of PML.

Serum samples were available from the three patients with confirmed PML obtained both before and after diagnosis. Only one patient, the patient with Crohn's Disease, had detectable JCV DNA in the serum prior to the onset of his symptoms. The other two patients had no detectable JCV DNA despite being clinically symptomatic for the disease and manifesting changes on a brain MRI scan. The observations in these groups of patients are consistent with the data from the literature demonstrating that the mere presence of JCV DNA in plasma is neither predictive nor diagnostic of PML.

In summary, the comprehensive safety assessment performed following the identification of PML in natalizumab-treated patients uncovered no additional confirmed cases of PML in the over 3,000 patients examined. Nearly all patients who had received natalizumab in recent MS, Crohn's Disease, and rheumatoid arthritis studies were accounted for during the assessments, making it unlikely that any cases of PML were missed. The occurrence of PML was limited to two MS cases and one Crohn's Disease case, as originally described. The incidence of PML in subjects treated with natalizumab in MS and Crohn's Disease clinical trials is therefore approximately 1/1,000 with a 95% confidence interval ranging from 0.2 to 2.8/1,000. Plasma testing proved to be neither predictive nor diagnostic of PML, consistent with the published literature (Kitamura et al., *J. Infect. Dis.* 161:1128-1133 (1990); Tornatore et al., *Ann. Neurol.* 31:454-462 (1992); Dorries et al., *Virology* 198:59-70 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9 (Suppl 1):81-87 (2003)). Clinical and MRI abnormalities were present in two of the three patients with PML before JCV DNA was detected in the plasma. In addition, JCV DNA was detected in plasma in several subjects in the study who had no clinical or radiographic signs of PML, including three who had never received natalizumab. These results suggest that establishing one static level of plasma JCV is not useful in predicting the likelihood of PML in asymptomatic patients. Physicians and patients should remain vigilant for signs and symptoms of PML and have a low threshold to suspend treatment and initiate appropriate diagnostic work-up (MRI, CSF analysis) in natalizumab-treated patients presenting with new neurological decline.

Consequences of Stopping Therapy

The consequences of stopping natalizumab therapy were carefully evaluated in a Phase 2 study, which involved 213 patients randomized to receive six monthly infusions of placebo, 3 mg/kg natalizumab, or 6 mg/kg natalizumab. Patients were followed for seven months after the last infusion. During that time, relapses and other adverse events were recorded, and MRI scans were performed four months and seven months after the last dose of natalizumab. Comparisons were made between the placebo group and the two natalizumab dosing groups. As expected, the proportion of patients experiencing relapse, as well as the frequency of relapses, rose in the natalizumab group to levels comparable to those in the placebo group after the cessation of study drug. Moreover, there was a gradual rise in the proportion of active MRI scans in the natalizumab group to levels comparable to that of the placebo group after the cessation of therapy. Thus, the cessation of natalizumab treatment resulted in loss of efficacy, but there was no evidence of an increase in disease activity beyond that which would have been expected had there been no treatment with natalizumab, i.e., no rebound effect was observed. Therefore, MS patients who discontinue natalizumab therapy do not have an increased risk for marked increase in disease activity.

Drug Interactions

In a placebo-controlled MS study, the administration of AVONEX® appeared to be associated with an increase in the serum concentrations of natalizumab in a small cohort on whom intensive pharmacokinetic sampling was performed. However, based upon a comparison of the mean post-hoc parameter estimates from the population pharmacokinetic analysis, steady-state clearance and half-life values differed between patients concurrently taking AVONEX® and natalizumab monotherapy, but only by approximately 5%, and were not considered clinically significant. In addition, natalizumab was well tolerated when administered to 589 patients in combination with AVONEX® for up to 120 weeks. It is notable that the two reports of PML in the MS database occurred in patients receiving concomitant AVONEX®. Thus, the risk of PML with natalizumab treatment may be increased by concomitant treatment with interferon β, though this could have occurred in two patients on combination therapy due to chance alone (p=0.23).

The safety of natalizumab in combination with glatiramer acetate was evaluated by administering natalizumab over six months to patients who continued to receive 20 mg of daily glatiramer acetate. There were no interactions between glatiramer acetate and natalizumab pharmacokinetics or its α4-integrin receptor saturation. However, this study was of insufficient size or duration to establish the long-term safety or efficacy in this population.

Efficacy of Natalizumab

Multiple Sclerosis

MS is a chronic disease of the brain and spinal cord. In temperate zones such as the United States, the incidence of MS is approximately 1 to 5/100,000 per year (US National MS Society; NMSS), with a US prevalence estimated at 350,000 to 400,000. It is a disease of young adults, primarily women, with disease onset typically occurring between the ages of 20 and 40. The first clinical manifestations of MS usually take the form of a clinically isolated syndrome affecting the optic nerve (optic neuritis), spinal cord (transverse myelitis), or brainstem/cerebellum (Runmarker and Anderson, *Brain* 116:117-134 (1993)). Estimates of the number of patients who eventually go on to develop MS vary widely, but, in the case of optic neuritis, the presence of MS-like lesions on MRI at the time of the attack indicates a greater than 80% chance of developing clinically definite MS within 10 years (O'Riordan et al., *Brain* 121:495-503 (1998); Sailer et al., *Neurology* 52:599-606 (1999)).

Demyelination and nerve fiber transection is thought to occur when activated T lymphocytes cross the blood-brain barrier and initiate a series of events leading to activation of endothelial cells, recruitment of additional lymphocytes and monocytes, and release of pro-inflammatory cytokines. MS lesions typically consist of immune cells, demyelinated axons, oligodendrocytes attempting remyelination, proliferating astrocytes, and varying degrees of axonal transection. Cytokines such as tumor necrosis factor-alpha (TNF-α) and interferon gamma (IFN-γ) interact with immune cells, amplifying this process. The initiating event of the inflammatory cascade is unknown; however, adhesion and trans-endothelial migration of inflammatory cells from the bloodstream across the blood-brain barrier and into the central nervous system (CNS) is thought to be an early and critical step in this process.

Emerging data demonstrate that irreversible axonal loss occurs early in the course of MS. Because transected axons fail to regenerate in the CNS, early effective treatment aimed at suppressing MS lesion formation is of paramount importance. As early as disease onset, axons are transected in lesions with active inflammation (Trapp et al., *N. Engl. J. Med.* 338:278-285 (1998); Bjartmar and Trapp, *Curr. Opin. Neurol.* 14:271-278 (2001); Ferguson et al., *Brain* 120 (Pt 3):393-399 (1997)). The degree of demyelination is related to the degree of inflammation and the exposure of demyelinated axons to the inflammatory environment, as well as non-inflammatory mediators (Trapp et al., *N. Engl. J. Med.*; 338:278-285 (1998); Kornek et al., *Am. J. Pathol.* 157:267-276 (2000); Bitsch et al., *Brain* 123:1174-1183 (2000)). There is also destruction of oligodendrocytes with impaired remyelination in demyelinating lesions (Peterson et al., *J. Neuropathy Exp. Neurol.* 61:539-546 (2002); Chang et al., *J. Neurovirol.* 8:447-451 (2002)). The loss of oligodendrocytes leads to a reduction in the capacity to remyelinate and may result in the loss of trophic factors that support neurons and axons (Bjartmar et al., *J. Neurocytol.* 28:383-395 (1999)).

The typical inflammatory lesions of MS can occur throughout the CNS, but certain sites seem particularly vulnerable, such as the optic nerve, brainstem, spinal cord, and periventricular regions of the cerebrum. It is the resulting loss of myelin and nerve fibers in these areas that leads to impaired neuronal conduction and symptoms such as weakness, sensory loss, visual loss, double vision, and imbalance. In relapsing remitting MS, these episodes of demyelination typically result in several weeks of neurological dysfunction followed by partial or full recovery. However, more severe attacks may result in permanent deficits. The recurrent attacks over time lead to accumulating physical disability and cognitive decline.

A number of measures, including clinical measures, those based on MRI scans, and those based on quality of life, can be used to assess a product's efficacy in treating MS. The Expanded Disability Status Scale (EDSS) is an extensively used tool for tracking the course of disability in MS. It classifies the most common MS-associated neurological impairments into disability levels ranging from 0 to 10, with each successive step describing a worsening of disease. In the lower range of the EDSS scale, disease progression is primarily defined by increasing levels of disability in specific functional systems measured during neurological examination. Scores of 1.0 through 3.5 describe mild to moderate disability in the functional systems. Higher scores, in the range of 4.0 and above indicate increasingly severe disability that affects ambulation, including the need for assistive devices such as a cane (an EDSS of 6.0), a walker (an EDSS of 6.5), or a wheelchair (an EDSS of 7.0). Scores higher than 7.0 classify patients confined to bed.

The MS Functional Composite (MSFC) (Whitaker et al., *Multiple Sclerosis* 1:37-47 (1995)) is also used to assess efficacy. Unlike traditional MS clinical outcome measures that are derived from the standard neurological examination, the MSFC is based on quantitative tests of leg function/ambulation (the Timed 25-Foot Walk), arm function (the Nine-Hole Peg Test), and cognitive function (the Paced Auditory Serial Addition Test (PASAT 3)) which expand upon the measurements of the EDSS and assess effects in clinical dimensions not well captured by this scale.

MRI is another tool for assessing efficacy in treating MS and can be used alone or to support clinical data to assess therapeutic effects on relapse and disability endpoints. MRI is a sensitive tool for monitoring disease activity, detecting approximately five to ten times more disease activity in both relapsing remitting MS and secondary progressive MS patients than is clinically apparent (Isaac et al., *Neurology* 38:1511-1515 (1988); Willoughby et al., *Ann. Neurol.* 25:43-44 (1989); Khoury et al., *Neurology* 44:2120-2124 (1994); Thompson et al., *Ann. Neurol.* 9:53-62 (1991); Thompson et al., *Neurology* 42:60-63 (1992)). T2-weighted sequences in MS patients detect new areas of acute demyelination, as well as more chronic areas of demyelination and gliosis. For this reason, T2-weighted MRI is a good technique for monitoring the accumulation of lesions over time, either as a count of active lesions or a change in the total volume of such lesions.

Infusion of gadolinium-diethylenetriamine pentaacetic acid (Gd-DPTA) during acquisition of T1-weighted sequences allows for visualization of blood-brain barrier breakdown secondary to the inflammation characteristic of acute MS lesions. The evidence to date suggests that gadolinium (Gd)-enhancement is a useful marker of disease activity that correlates with clinical relapse (Molyneux et al., *Ann. Neurol.* 43:332-339 (1998); Kappos et al., *Lancet* 353:964-969 (1999); McFarland et al., *Multiple Sclerosis* 8:40-51 (2002)).

New hypointense lesions on T1-weighted sequences in MS patients correspond either with inflammatory Gd-enhancing lesions (comprising edema, demyelination, axonal loss, or combinations of these pathologies) (Bruck et al., *Ann. Neurol.* 42:783-793 (1997)) or as chronic lesions with considerable axonal loss. Approximately half of the acute T1 hypointensities on MRI will evolve into chronic "T1 black holes," which correlate with disability progression (Simon et al., *Neurology* 55:185-192 (2000)).

As described in more detail in Example 1, two Phase 3 studies were conducted to study the effect of two years of treatment with natalizumab. One of the studies used natalizumab alone (the monotherapy study) and the other used natalizumab in combination with AVONEX® (the add-on therapy study). Both these Phase 3 studies were designed with two sets of primary and secondary endpoints. The primary and secondary endpoints were selected to measure the effects of natalizumab on the inflammatory aspects of the disease after a mean of one year of follow-up in each study (900 patient-years of observation in the monotherapy study; 1,200 patient-years in the add-on therapy study).

The primary endpoint of these studies was the annualized rate of clinical relapses. Two of the secondary endpoints were two supporting MRI measures of inflammatory disease activity, namely, the mean number of new or newly enlarging T2-hyperintense lesions (measuring lesion accumulation over time) and the mean number of Gd-enhancing lesions (measuring acute disease activity), as ranked in order of importance. The proportion of patients remaining relapse-free provided a third secondary endpoint.

Another series of endpoints was assessed at the conclusion of each study following two years of natalizumab treatment. The endpoints for this final analysis were selected to determine natalizumab's effects on measures associated with MS disease progression. The primary endpoint at two years was the time until onset of sustained progression of disability, as measured by changes in EDSS scores. Similar to the one-year analysis, the secondary endpoints were additional MRI and clinical measures that would support the primary analysis. The secondary endpoints at two years, ranked in order of importance, were the rate of MS relapses (to confirm one-year relapse observations), the mean volume of T2-hyperintense lesions (a measure of overall MS disease burden), the mean number of T1-hypointense lesions (a measure of axonal loss), and progression of disability as determined by changes in the MSFC (to confirm and expand upon disability effects as measured by the EDSS).

Given two primary endpoints at two different time points (annualized relapse rate at one year, time to disability progression at two years), the Hochberg procedure for multiple comparisons (Hochberg, Biometrika 75:800-802 (1988)) was used to evaluate the primary endpoint. Each set of secondary endpoints was prioritized in order of importance as listed above. A closed testing procedure was used for each set, such that if statistical significance was not achieved for an endpoint within a set, all endpoints(s) of a lower rank in that set were not considered statistically significant. Analyses of tertiary endpoints did not include adjustments for multiple comparisons.

Monotherapy with Natalizumab

These results of the monotherapy study indicated that natalizumab is an effective treatment as monotherapy for relapsing remitting MS. Natalizumab treatment resulted in significant effects on relapse rates, disability progression, and all MRI measures, the primary and secondary endpoints of the study. Analysis of Kaplan-Meier curves indicate that the impact on relapse rates and disability progression was apparent early after treatment initiation, and was sustained throughout the treatment period with patient groups continuing to diverge at the final timepoint. Further, these findings were consistent across subgroups. Additional positive effects were seen on measures of relapse severity and quality of life.

MS patients treated with natalizumab alone had a 42% lower risk of their disability progressing compared to placebo, as measured by changes on the EDSS, the primary endpoint of the study at two years ($p<0.001$). The percentage of patients estimated to progress was 17% and 29% with natalizumab and placebo, respectively. In addition to the EDSS, natalizumab had significant effects on all relapse endpoints studied over two years, including a 68% reduction in the annualized relapse rate compared to placebo, with 67% of natalizumab-treated patients remaining relapse-free, compared to 41% of patients on placebo. The MRI scans supported these clinically-observed effects. Also, natalizumab treatment improved the patients' quality of life, as measured by the physical and mental components of the SF-36. All these effects were consistent and significant across subgroups defined by baseline demographics and disease activity.

Combination Therapy of Natalizumab and AVONEX®

A significant number of patients who receive the currently approved therapies continue to experience disease activity, as measured both clinically and by MRI. This is an expected outcome of these partially effective approved medications, each of which leads to an approximately 30% reduction in relapse rate (IFNB MS Study Group, Neurology 43:655-661 (1993); Jacobs et al., Ann. Neurol. 39:285-289 (1996); PRISMS Study Group, Lancet 352:1498-1504 (1998); Johnson et al., Neurology 45:1268-1276 (1995)). Data from the Phase 3 trials of β-interferon for the treatment of MS show that 62% to 75% of patients experienced at least one relapse during these two-year trials despite interferon treatment IFNB MS Study Group, Neurology 43:655-661 (1993); Jacobs et al., Ann. Neurol. 39:285-289 (1996); PRISMS Study Group, Lancet 352:1498-1504 (1998)). Similarly, 66% of subjects in the Phase 3 MS trial of glatiramer acetate experienced at least one relapse during the 2-year period, a number that was not significantly different from placebo (Johnson et al., Neurology 45:1268-1276 (1995)). Although a variety of therapeutic strategies are currently in use in clinical practice to manage breakthrough disease while on treatment (e.g., switching therapy, changing dose and frequency of interferon, combination therapy), these practices are largely empirical as there are no randomized, controlled trials to assess the efficacy of these approaches.

The add-on therapy study was designed to evaluate the efficacy of natalizumab against active control for patients breaking through AVONEX® monotherapy. The choice of β-interferon was supported by available data on the proposed mechanisms of action of the available drugs. As discussed above, natalizumab has a well-defined mechanism of action, specifically targeting cellular adhesion and trans-endothelial migration via α4-integrins. Although the exact mechanism by which interferon-β exerts efficacy in MS is not known, interferon-β induces a large number of cellular processes involved in cytokine secretion and cellular phenotype changes. Interferon-β down regulates interferon-γ induced MHC class II molecule production, decreases secretion of TH1 pro-inflammatory cytokines (TNF-α, IL-2 and interferon-γ) and increases secretion of TH2 anti-inflammatory cytokines (IL-4 and IL-10) (Rep et al., J. Neuroimmunol. 67:111-118 (1996); Kozovska et al., Neurology 53:1692-1697 (1999); Rudick et al., Neurology 50:1266-1272 (1998)). In addition, interferon-β may affect leukocyte trafficking through suppression of the chemokines RANTES and MIP-1α, as well as their receptor CCR5 (Zang et al., J. Neuroimmunol. 112:174-180 (2001)). There is, therefore, scientific rationale to expect that the blockade of α4-integrins by natalizumab, when added to interferon-β, may have an additive or synergistic effect when added to interferon-β alone.

Natalizumab was also proven efficacious when used to treat patients concurrently receiving treatment with AVONEX®. Prior to receiving natalizumab, these patients were experiencing disease activity despite active treatment. Thus, AVONEX® served as an active control. The study demonstrated that natalizumab, when added to AVONEX®, resulted in a 24% reduction in the risk of disability progression, as measured by changes on the EDSS ($p=0.024$). The percentage of patients estimated to progress was 23% with natalizumab plus AVONEX® as compared with 29% on AVONEX® alone.

Natalizumab had significant effects on all relapse endpoints examined, when compared to AVONEX® over two years, including a 55% reduction in the annualized relapse rate, with 54% of natalizumab-treated patients relapse-free compared to 32% of patients on AVONEX®. The MRI scans supported these clinically-observed effects. Also, natalizumab, when compared to AVONEX® therapy alone, improved the patients' quality of life, as measured by the physical components of the SF-36, with a trend on the mental component. All these effects were consistent and significant across subgroups defined by baseline demographics and disease activity.

Progressive Multifocal Leukoencephalopathy

PML is an infectious disease of the central nervous system caused by JCV infection of oligodendrocytes. JCV is a human polyoma virus that is believed to infect the majority of healthy individuals at an early age. The seroprevalence of anti-JCV antibodies in healthy individuals has been estimated to range from 20% to 80% depending upon the testing methodology (Knowles et al., *J. Med. Virol.* 71:115-123 (2003)); Knowles and Sasnauskas, *J. Virol. Methods.* 109: 47-54 (2003)).

PML occurs predominantly in immunocompromised individuals with an age-adjusted death rate due to PML of 3.3 per million persons (in 1994), 89% of whom were AIDS patients (Holman et al., *Neuroepidemiol.* 17:303-309 (1998)). However, rare PML cases have also been reported in patients with autoimmune disorders who received immunosuppressive therapy; among these, three patients with rheumatoid arthritis (Sponzilli et al., *Neurology* 25:664-668 (1975); Rankin et al., *J. Rheumatol* 22:777-79 (1995); Durez et al., *Arthritis Rheum.* 46 (9S):536 (2002)), one of whom was treated with tumor necrosis factor (TNF) antagonist (Durez et al., *Arthritis Rheum.* 46 (95):536 (2002)). There was also a report of PML in a Crohn's Disease patient, but the concomitant treatments were not specified (Garrels et al., *Am. J. Neuroradiol.* 17:597-600 (1996)).

The pathology of PML is distinctive and comprises multiple foci of demyelination of varying size from pinpoint lesions to areas of several centimeters. The lesions may occur anywhere but are usually in the cerebral hemispheres, less often in the cerebellum and brain stem and rarely in the spinal cord. The oligodendrocytes in the peripheral zone surrounding an area of demyelination are grossly abnormal. The nuclei of abnormal oligodendrocytes are packed with JC virions. Typically, PML evolves gradually, with impairment of mental function and disturbance of speech and vision. Movement may also be affected. The disease then progresses rapidly and the patient is severely disabled, eventually becoming demented, blind, and paralyzed; coma and death follow.

The presence of JCV in the blood and urine of PML patients and healthy, immunocompetent individuals has been described (Kitamura et al., *J. Infect. Dis.* 161:1128-1133 (1990); Tornatore et al., *Ann. Neurol.* 31:454-462 (1992); Dorries et al., *Virology* 198:59-70 (1994); Sundsfjord et al., *J. Infect. Dis.* 169:485-490 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9(Suppl 1):81-87 (2003)). These findings are neither predictive nor diagnostic of PML in these patients; thus the relationship of blood or urine viral load to PML is unclear.

The clinical presentation of PML is largely dependent upon the size and distribution of the white matter lesions that develop as a result of viral infection, demyelination, and glial cell lysis. However, clinical features of the presentation help differentiate it from the demyelination associated with MS. In contrast to MS, PML involvement of the spinal cord or optic nerves is rare. Instead, about one-third of patients will present with visual field loss or cortical blindness with another third presenting with altered mentation or behavior changes (Dworkin et al., *Curr. Clin. Top. Infect. Dis.* 22:181-195 (2002)). Also unlike MS, hemiparesis is a common presenting symptom. These symptoms are typically sub-acute in onset and follow a slowly progressive course. Often, patients and their families are the first to notice the onset of PML through changes in the ability to perform routine activities of daily living, even prior to presentation with changes on neurological examination.

MRI is a sensitive tool for the detection of PML lesions in the setting of clinical signs or symptoms, although it may lack specificity. Typical MS lesions, demyelination from other causes (e.g., encephalomyelitis, HIV encephalopathy), gliosis, and edema can often have an appearance similar to early PML lesions. However, as shown in Table 1, there are features of PML lesions that help differentiate them from other etiologies (Post et al., *Am. J. Neuroradiol.* 20:1896-1906 (1999); Yousry et al. *N. Engl. J. Med.* in press (2006); (Berger et al., *Ann. Neurol.* 44:341-349 (1998); Hoffmann et al., *J. Neurol. Neurosurg. Psychiatry* 74:1142-1144 (2003); Langer-Gould et al., *N. Engl. J. Med.* 353:375-381 (2005)).

TABLE 2

Differential Diagnosis of MS and PML

| | MS | PML |
|---|---|---|
| Location of new lesions | Mostly focal, may affect entire brain and spinal cord, in white and possibly gray matter; | Diffuse, mainly sub-cortical, rarely periventricular, almost exclusively in white matter, although occasional extension to gray matter seen; |
| | Posterior fossa lesions rarely seen | Posterior fossa frequently involved (cerebellum) |
| Borders | Sharp edges, shapes mostly round or finger-like (especially periventricular), confluent with other single lesions, U-fibers may be involved | Ill-defined edges, infiltrating, irregular in shape, confined to white matter, sparing gray matter, pushing against cortex, U-fibers destroyed |
| Mode of extension | Focal, enlarging of lesions within days/weeks, later decreasing in size within months | Diffuse, asymmetrical, extending homogeneously, no confluence with other lesions, defined to white matter tracks, sparing cortex, continuous progression |
| Mass effect | Acute lesions may show some mass effect | No mass effect even in large lesions (but process is slightly pushing against cortex) |
| T2-weighted sequence | Acute lesions: hyperintense center, isointense ring, discrete hyperintensity outside ring structure; Sub-acute/chronic lesions: hyperintense, no ring structure | Diffuse hyperintense, slightly increased intensity of newly involved areas compared to old areas, little irregular signal intensity of lesions |
| T1-weighted sequence | Acute lesions: densely hypointense (large lesion) or isointense (small lesion), increasing signal intensity over time in 80%, decreasing signal intensity (axonal loss) in about 20% | Slightly hypointense from the onset, signal intensity decreasing over time and along the affected area, no reversion of signal intensity |
| Flair sequence | Hyperintense, sharply delineated | Hyperintensity more obvious, true extension of abnormality more clearly visible than in T2-weighted images |

TABLE 2-continued

Differential Diagnosis of MS and PML

| | MS | PML |
|---|---|---|
| Enhancement | Acute lesions: dense homogeneous enhancement, sharp edges Sub-acute lesions: ring-enhancement Chronic lesions: no enhancement | Usually no enhancement even in large lesions, in HIV+ patients some peripheral enhancement possible, especially under therapy |
| Atrophy | Focal atrophy possible due to focal white matter degeneration, no progression | No focal atrophy since extending pathological process is slightly pushing against cortex (extension of tissue) |

MRI analysis can provide a differential diagnosis of MS and PML in patients receiving natalizumab. Patients suspected of PML demonstrate the presence of multifocal, asymmetric, white-matter lesions reflective of demyelination by MRI. $T_2$-weighted and fluid-attenuated inversion recovery (FLAIR) MRI reveals hyperintense lesions throughout the supratentorial subcortical white matter (Post et al., *Am. J. Neuroradiol.* 20:1896-1906 (1999)). White matter lesions of PML are typically not surrounded by edema, do not produce a mass effect, and do not enhance in the presence of gadolinium contrast material (Post et al., *Am. J. Neuroradiol.* 20:1896-1906 (1999)). However, hyperintense $T_2$-weighted and FLAIR images are not specific for demyelination and may represent gliosis or edema. Other demyelinating, encephalopathic or ischemic processes such as MS, postviral encephalitis, HIV encephalopathy and infarction, may demonstrate similar non-specific imaging features (Olsen et al., *Radiology* 169:445-448 (1988), Hurley et al., *J. Neuropsychiatry Clin. Neurosci.* 15:1-6 (2003)). The location of lesions and their morphological characteristics, the absence or an atypical presence of gadolinium enhancement on $T_1$-weighted images, and the implementation of magnetization transfer MRI may also help differentiate the demyelination of PML from other demyelinating processes, edema or gliosis (Ernst et al., *Radiology* 210:439-543 (1999); Hurley et al., *J. Neuropsychiatry Clin. Neurosci.* 15:1-6 (2003)).

The clinical diagnosis of PML is confirmed by histological and virological examination of brain material obtained by brain biopsy or at postmortem. Before a biopsy is done, both serum and CSF should be examined for antibodies against JCV. A positive result will not confirm PML, but a negative result makes the diagnosis of PML very unlikely. It is rare to detect antibodies against JC in the CSF, and when they are detected, it is suggestive of active multiplication of JCV within the CNS. The brain biopsy or autopsy material can be examined by electron microscopy or immunohistologic electron microscopy. The specimen can also be examined directly for JCV antigen by immunofluorescence or immunoperoxidase staining. Viral isolation of JCV has been reported to be difficult, but may be attempted from primary human fetal glial cells. The presence of the virus in culture is confirmed by electron microscopy, immunofluorescence, or haemagglutination.

PCR analysis of the CSF for JC viral DNA is a highly sensitive and specific test for the diagnosis of PML. The specificity of this test approaches 100%, with a sensitivity ranging from 60% to 90% (Henson et al., *Neurology* 41:1967-1971 (1991); Gibson et al., *J. Med. Virol.* 39:278-281 (1993); Weber et al., *AIDS* 8:49-57 (1994a); Weber et al. *J. Infect. Dis.* 169:1138-1141 (1994b); Vago et al., *J. Acquir. Imm. Defic. Syndr. Hum. Retrovirol.* 12:139-146 (1996)). In cases with a high clinical suspicion of PML and negative CSF results, repeat testing often leads to detection of JC viral DNA. As such, PCR analysis of the CSF for JC viral DNA has grown to be the preferred method to confirm the diagnosis of PML.

Untreated, PML patients have a mortality rate of 30% to 50% during the first three months (Koralnik, *Curr. Opt. Neurol.* 17:365-370 (2004)). Prior to the introduction of highly active antiretroviral treatment (HAART) for HIV, about 10% of patients with PML survived for longer than one year. However, since the advent of HAART, about 50% of patients with PML survive for longer than one year due to restoration of immune function as CD4 counts increased as a result of immune reconstitution inflammatory syndrome (Geschwind et al., *J. Neurovirol.* 7:353-357 (2001); Berger et al., *Ann. Neurol.* 44:341-349 (1998); Clifford et al., *Neurology* 52:623-625 (1999); Tantisiriwat et al., *Clin. Infect. Dis.* 28:1152-1154 (1999)).

Currently, there is no established drug treatment for PML. Various medications have been tested, including acyclovir, idoxuridine, vidarabine, amantadine, adenine arabinoside, cytosine arabinoside (cytarabine), cidofovir, interferon α, interleukin-2 (IL-2), zidovudine, camptothecin, and topotecan (Koralnik, *Curr. Opt. Neurol.* 17:365-370 (2004); Dworkin et al., *Curr. Clin. Top. Infect. Dis.* 22:181-195 (2002); Seth et al., *J. Neurovirol.* 9:236-246 (2003); Collazos, *CNS Drugs* 17:869-887 (2003); Mamidi et al., *J. Neurovirol.* 8:158-167 (2002); Przepiorka et al., *Bone Marrow Transplant;* 20:983-987 (1997); Redington et al., *Arch. Neurol.* 59:712-718 (2002); Padgett et al., *Prog. Clin. Biol. Res.* 105:107-117 (1983)). However, the survival of patients with PML appears to be best correlated with immune reconstitution. In transplant patients with PML, early dosage reduction or/and discontinuation of immunosuppressive therapy was associated with favorable clinical outcome after PML diagnosis (Crowder et al., *Am. J. Transplant* 5:1151-1158 (2005); Shitrit et al., *Transpl. Int.* 17:658-665 (2005)).

JC Virus (JCV)

JCV is a member of the class of human polyomavirus, which belong to the Papovaviridae family of small, nonenveloped viruses with a closed, circular double DNA-stranded genome. Polyomaviruses can be distinguished from papillomaviruses by virtue of their smaller virion size and different genomic size and organization. Polyomaviruses are ubiquitous in nature and can be isolated from a number of species. JCV was first isolated from the brain tissue of a patient with progressive multifocal leukoencephalopathy (PML). JCV shares 75% nucleotide sequence homology with the BK human polyomavirus (BKV), which was isolated from the urine of a renal transplant patient with postoperative ureteral stenosis. BKV and JCV each share 70% homology with SV40. The two are not serologically cross-reactive and serologic tests for antibodies are able to distinguish between BKV and JCV (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406).

JCV infection is usually sub-clinical, is almost universal, occurs in childhood, and persists for life. It is estimated that 60-80% of adults in Europe and the United States have antibodies to JCV and that 50% of young adults in the age range of 30-39 years have been infected with JCV. JCV and BKV are believed to circulate independently. It has been proposed that JCV establishes latent infections in the kidney and/or the CNS after a primary infection (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406). During immunosuppression, it has been postulated that latent JCV is reactivated in the kidney, which may lead to viruria. While viruria may have some predictive value for PML, since it does not occur in the majority of PML cases, measuring JCV in the urine alone is not sufficient to diagnose JCV.

When JCV travels through the bloodstream to the brain, it may attack myelin-producing cells. The resulting brain infection produces neurological symptoms which may include ataxia, loss of cognitive function, visual loss, changes in balance and coordination, and loss of sensation. Death commonly occurs within two years following diagnosis.

No specific antiviral therapy that has been proven effective for JCV, and current treatment of immunocompromised patients is primarily supportive and intended to reduce immunosuppression. Cidofovir is currently being studied as a treatment option for transplant patients, and cytarabine can be used in the treatment of PML, although there is currently conflicting data regarding the efficacy of the latter (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406; Salmaggi, *Neurol. Sci.* 22:17-20 (2001)).

The cellular receptor for JCV has been reported to be the serotonin 5HT2(A) receptor (Elphick et al., *Science* 306: 1380-1383 (2004)). In vitro, the antipsychotic medications chlorpromazine and clozapine were shown to block the serotonin 5HT2(A) receptor and to block JCV cell entry. Unfortunately, however, chlorpromazine and clozapine have such significant side effects and toxicities, e.g., extrapyramidal symptoms and the possibility of bone marrow dyscrasias that they may be problematic to use clinically. The invention provides that newer atypical antipsychotics, such as zisprasidone, risperidone, and olanzapine—medicines with much better side effect and toxicity profiles than the older antipsychotics—are significantly more potent 5HT2 (A) receptor antagonists in vitro than chlorpromazine and clozapine.

A wide variety of serological tests are available to detect JCV, e.g., complement-fixation (CFT), haemagglutination-inhibition (HAI), enzyme-linked immunoassay (EIA), radioimmunoassay (RIA), particle agglutination, immuno-fluorescence (IF), single radial hemolysis, and Western blot. The sensitivity and specificity varies greatly between different techniques. Most techniques will detect all classes of antibody, whereas some assays e.g., RIA, EIA, and IF can be designed to detect one specific class, for example, IgM, IgG, or IgA.

Patient Selection Based on Safety and Efficacy

Appropriate patient selection helps maximize the benefit-risk profile of natalizumab. Natalizumab has demonstrated efficacy in treatment-naïve patients with mild to moderate disability (EDSS 0 to 5.0) with recent clinical disease activity (for example, one relapse in the year prior to study entry). It has also demonstrated efficacy in patients with mild to moderate disability with continuing disease activity despite treatment with β-interferon (for example, one relapse in the year prior to study entry, while receiving AVONEX®).

The benefit/risk ratio is altered in certain other patient populations. Patients without evidence of relapsing disease, that is, without evidence of inflammatory activity clinically or by MRI, such as those with relatively "benign" inactive disease, or chronic-progressive forms of MS, were excluded from the Phase 3 trials, thus, natalizumab has not been completely evaluated in these cohorts. The benefit-risk is also altered in patients with a single clinical event without features suggestive of MS.

Patients who are clinically stable on current therapy also have an altered benefit/risk ratio. If safety or tolerability concerns exist on the current treatment, or imaging studies indicate active inflammatory sub-clinical disease, natalizumab treatment would be appropriate. In considering the benefit-risk ratio, it should be considered whether the patient has previously suffered a hypersensitivity reaction or developed persistent antibodies to natalizumab. Re-dosing of natalizumab following a hypersensitivity reaction was not assessed in Phase 3 trials. Persistent antibodies against natalizumab lead to a loss of efficacy and an increase in infusion-related side effects. Patients who are immunocompromised from any cause, including use of immunosuppressant medications have an independent risk factor for PML and other opportunistic infections and should not receive natalizumab.

Another criteria for patient selection is a pre-infusion checklist used by the infusion nurse to facilitate early detection of PML and minimize inappropriate use of natalizumab. The checklist prompts the nurse to ask the patient about continuously worsening neurological symptoms that have persisted over several days, e.g., new or sudden decline in thinking, eyesight, balance, or strength. If a patient reports having any symptoms described by the checklist, the nurse is instructed not to administer natalizumab and to refer the patient to his or her physician.

This checklist also ascertains that the patient will be receiving natalizumab for the treatment of relapsing MS, has never been diagnosed with PML, and is not currently experiencing any continuously worsening symptoms that have persisted over several days. It further ascertains that the patient is not known to be suffering from HIV or a hematologic malignancy, nor has had an organ transplant. It confirms that the patient is not currently receiving treatment with an anti-neoplastic, immunomodulatory, or immunosuppressive agent and that the patient has read the natalizumab patient information leaflet.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. The specification is most thoroughly understood in light of the references cited herein.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Efficacy of Natalizumab

The efficacy of natalizumab over a two year period has been demonstrated in two Phase 3 trials (Polman et al., *N. Engl. J. Med.* in press (2006); Rudick et al. *N. Engl. J. Med.* in press (2006)). In one study, natalizumab was given as monotherapy to treatment-naïve MS patients and its efficacy was compared to placebo. In the other study, natalizumab was given to patients who were experiencing relapses despite concurrent AVONEX® therapy and its efficacy was compared to that of AVONEX (interferon β-1a) plus placebo. Data through two years have confirmed the benefit that led to accelerated approval at one year. These data show that natalizumab is highly efficacious in delaying the time to onset of sustained progression of disability, in reducing annualized relapse rate, in attenuating MRI lesions, and in improving the quality of life of patients compared both to placebo and the active AVONEX® control group.

Both Phase 3 studies had similar designs. In the monotherapy study, 942 untreated relapsing remitting MS patients were randomized to receive natalizumab or placebo for 120 weeks (30 infusions) using a 2:1 allocation. In the add-on study, 1,171 patients who had been receiving weekly intramuscular injections of 30 μg AVONEX®, but who had relapsed despite this treatment, were randomized using a 1:1 allocation to add natalizumab or placebo to their regimen, also for 120 weeks.

Efficacy parameters included EDSS scores, MS relapses, brain MRI scans, MSFC scores, visual function tests, and quality of life. EDSS and MSFC were measured every 12 weeks, brain MRI scans and quality of life questionnaires at baseline and every year, and MS relapses on an ongoing basis.

Treatment with natalizumab as monotherapy in treatment-naïve patients had profound effects on the time to onset of sustained progression in disability and on annualized relapse rate, the two primary endpoints, as shown in Table 2. These significant effects were confirmed versus AVONEX® alone.

TABLE 2

Efficacy of Natalizumab in Phase 3 Studies

| | Monotherapy | | Add-on therapy | |
| --- | --- | --- | --- | --- |
| | Placebo | 300 mg natalizumab | AVONEX + placebo | AVONEX + 300 mg natalizumab |
| Number of patients | 315 | 627 | 582 | 589 |
| Percentage of patients with sustained progression of disability | 29% | 17% | 29% | 23% |
| Hazard ratio (95% confidence interval) | 0.58 (0.43, 0.77) | | 0.76 (0.61, 0.96) | |
| Risk reduction | 42% | | 24% | |
| p-value | $p < 0.001$ | | $p = 0.024$ | |
| Annualized relapse rate | 0.733 | 0.235 | 0.749 | 0.336 |
| Relative reduction | 68% | | 55% | |
| p-value | $p < 0.001$ | | $p < 0.001$ | |

The patient population in the two Phase 3 studies were relapsing MS patients according to the criteria of the International Panel on the Diagnosis of Multiple Sclerosis (McDonald et al., *Ann. Neurol.* 50:121-127 (2001)). It encompassed a broad range of ages and disease severity, and represented the current relapsing MS population with active disease, consistent with the approved indication. Patients with primary- or secondary-progressive MS were excluded.

The patient populations targeted for the two studies differed. Patients in the monotherapy study were essentially naïve to treatment with an immunomodulatory drug for MS. Specifically, patients may not have had treatment with any immunomodulator (n-interferon or glatiramer acetate) for a period longer than six months and not within six months of the beginning of the study. The result was a young, mostly female, MS population with a moderate degree of baseline disease activity (typical of the general MS population), very few of whom had tried another immunomodulator prior to study entry.

Patients in the add-on therapy study were required to have received AVONEX® for the previous year and to have had a relapse during that time while on AVONEX® treatment. This resulted in a population somewhat older than that in the monotherapy study, with a longer disease duration. However, patients in the add-on therapy study had a similar degree of diseaseactivity as those in the monotherapy study, despite AVONEX® treatment.

The invention claimed is:

1. A method of treating a patient with multiple sclerosis or Crohn's disease with natalizumab comprising:
   (a) detecting an amount of endogenous IgG4 in the patient's plasma or serum prior to initiating treatment; and
   (b) administering a dose of natalizumab to the patient for a dosage period, wherein the dose is lower than 300 mg by IV infusion and/or the dosage period is longer than four weeks and the amount of endogenous IgG4 detected is below 200 µg/mL.

2. The method of claim 1, wherein the administered dose of natalizumab is below 300 mg by IV infusion.

3. The method of claim 1, wherein the amount of IgG4 in the patient's blood is below 200 µg/ml and the administered dose of natalizumab is administered for a dosage period longer than four weeks.

4. The method of claim 1, further comprising monitoring the patient for indicators of serious infection and/or treating the patient with prophylaxis designed to reduce the risk of developing serious infection.

5. The method of claim 1, further comprising monitoring the patient for indications of progressive multifocal leukoencephalopathy.

6. The method of claim 5, wherein the monitoring detects JCV in the patient's urine, blood, and/or cerebrospinal fluid.

7. The method of claim 5, wherein the monitoring comprises testing for clinical and/or radiologic symptoms of progressive multifocal leukoencephalopathy.

8. The method of claim 5, further comprising, in the presence of indicators of progressive multifocal leukoencephalopathy, providing at least one treatment selected from intravenous immunoglobulin therapy, plasmapheresis, and antiviral therapy.

9. A method of inhibiting binding between an α4-integrin expressed on a leukocyte and one or more molecules selected from VCAM-1, MAdCAM-1, osteopontin, and fibronectin in a patient comprising
   (a) detecting an amount of endogenous IgG4 in the patient's plasma or serum prior to initiating treatment with natalizumab; and
   (b) administering a dose of natalizumab to the patient for a dosage period, wherein the dose is lower than 300 mg by IV infusion and/or the dosage period is longer than four weeks and the amount of endogenous IgG4 detected is below 200 µg/mL.

10. The method of claim 9, wherein the administered dose of natalizumab is below 300 mg by IV infusion.

11. The method of claim 9, wherein the amount of IgG4 in the patient's blood is below 200 µg/ml and the administered dose of natalizumab is administered for a dosage period longer than four weeks.

12. The method of claim 9, further comprising monitoring the patient for indicators of serious infection and/or treating the patient with prophylaxis designed to reduce the risk of developing serious infection.

13. The method of claim 9, further comprising monitoring the patient for indications of progressive multifocal leukoencephalopathy.

14. The method of claim 13, wherein the monitoring detects JCV in the patient's urine, blood, and/or cerebrospinal fluid.

15. The method of claim 13, wherein the monitoring comprises testing for clinical and/or radiologic symptoms of progressive multifocal leukoencephalopathy.

16. The method of claim 13, further comprising, in the presence of indicators of progressive multifocal leukoencephalopathy, providing at least one treatment selected from intravenous immunoglobulin therapy, plasmapheresis, and antiviral therapy.

17. The method of claim 5, wherein the monitoring comprises serially removing samples of the patient's blood, measuring the amount of IgG antibodies to JCV in the samples, and comparing the amount of the antibodies in the samples.

18. The method of claim 13, wherein the monitoring comprises serially removing samples of the patient's blood, measuring the amount of IgG antibodies to JCV in the samples, and comparing the amount of the antibodies in the samples.

* * * * *